United States Patent [19]
Shinomiya et al.

[11] Patent Number: 5,447,162
[45] Date of Patent: Sep. 5, 1995

[54] ELECTRONIC SPHYGMOMANOMETER

[75] Inventors: Tsutomu Shinomiya; Takahiro Souma, both of Nakai, Japan

[73] Assignee: Terumo Kabushiki Kaisha, Tokyo, Japan

[21] Appl. No.: 1,585

[22] Filed: Apr. 19, 1993

Related U.S. Application Data

[62] Division of Ser. No. 800,073, Nov. 27, 1991, Pat. No. 5,218,967, which is a division of Ser. No. 591,410, Oct. 10, 1990, Pat. No. 5,103,830.

[30] Foreign Application Priority Data

| Oct. 5, 1989 | [JP] | Japan | 1-258797 |
| Oct. 5, 1989 | [JP] | Japan | 1-258798 |
| Oct. 9, 1989 | [JP] | Japan | 1-262189 |

[51] Int. Cl.⁶ .................................. A61B 5/00
[52] U.S. Cl. ................... 128/680; 128/681; 128/682
[58] Field of Search ............ 128/677, 680–687; 364/412.03

[56]        References Cited
U.S. PATENT DOCUMENTS

| 3,978,848 | 4/1976  | Yen et al. ............ 128/689 |
| 4,009,709 | 3/1977  | Link et al. . |
| 4,408,614 | 10/1983 | Weaver et al. ........ 128/680 |
| 4,592,365 | 6/1986  | Georgi .................. 128/680 |
| 4,677,983 | 7/1987  | Yamaguchi et al. .... 128/680 |
| 4,712,564 | 12/1987 | Yamaguchi . |
| 5,054,495 | 10/1991 | Uemura et al. . |
| 5,135,003 | 8/1992  | Souma ................... 128/680 |
| 5,140,991 | 8/1992  | Niwa .................... 128/687 |

FOREIGN PATENT DOCUMENTS

| 0154995   | 9/1985  | European Pat. Off. . |
| 0240924   | 10/1987 | European Pat. Off. . |
| 0378683   | 7/1990  | European Pat. Off. . |
| 56-34328  | 4/1981  | Japan . |
| 59-19691  | 5/1984  | Japan . |
| 61-79443  | 4/1986  | Japan . |
| 61-40416  | 9/1986  | Japan . |
| 63-171539 | 7/1988  | Japan . |
| 2165052   | 4/1986  | United Kingdom . |
| WO89/01310| 2/1989  | WIPO . |

Primary Examiner—Lee S. Cohen
Assistant Examiner—Robert L. Nasser, Jr.
Attorney, Agent, or Firm—Frishauf, Holtz, Goodman & Woodward

[57]                ABSTRACT

An electronic Sphygmomanometer employing both the Korotkoff method and the oscillometric method which is thereby capable of accurately measuring blood pressure due to the advantages of the two methods. The electronic sphygmomanometer is arranged in such a manner that either of the results of measurements of the two methods can be automatically selected. A gate for detecting the Korotkoff sound by using an oscillation in cuff pressure is automatically stopped, and the validity of the Korotkoff sound is determined in accordance with a change in the height of the oscillating pulse wave.

3 Claims, 23 Drawing Sheets

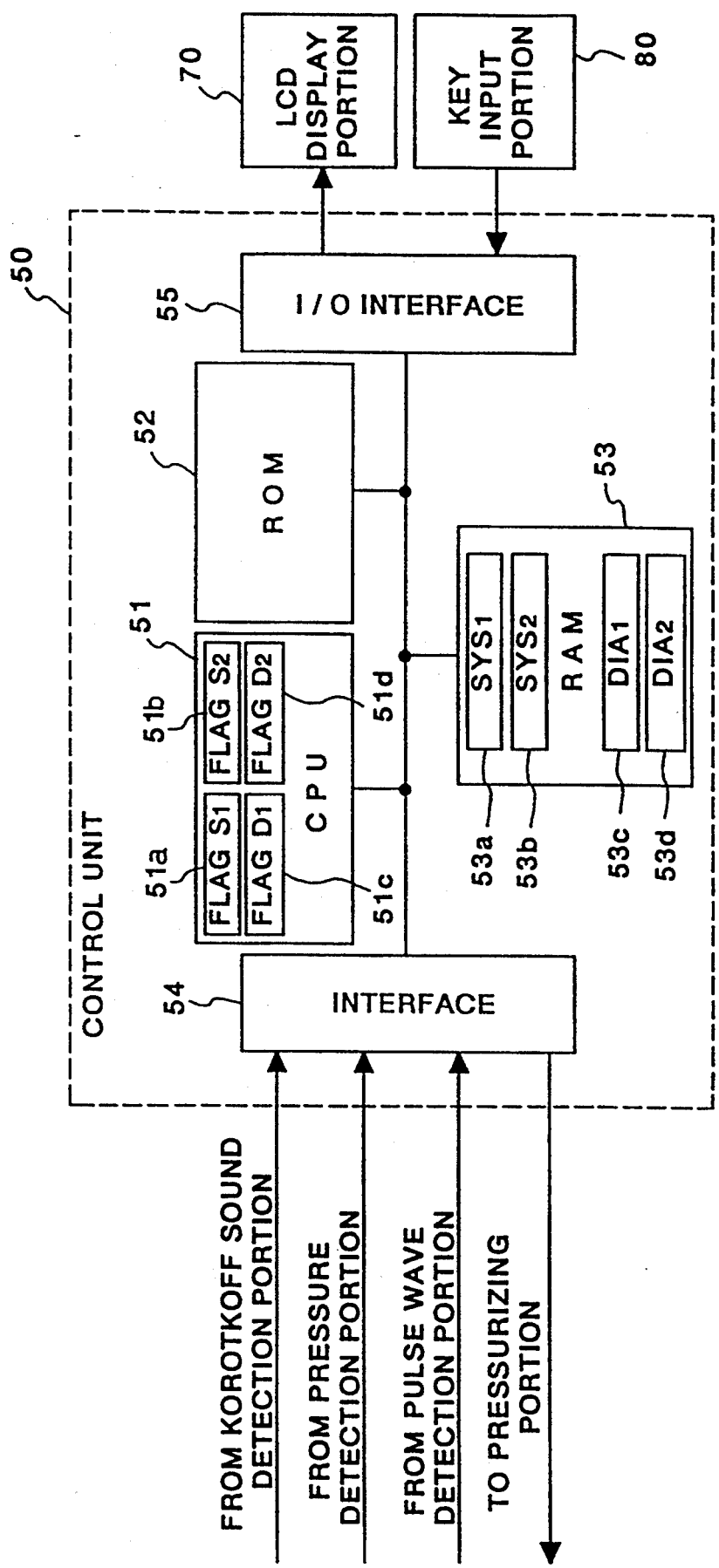
F I G. 5

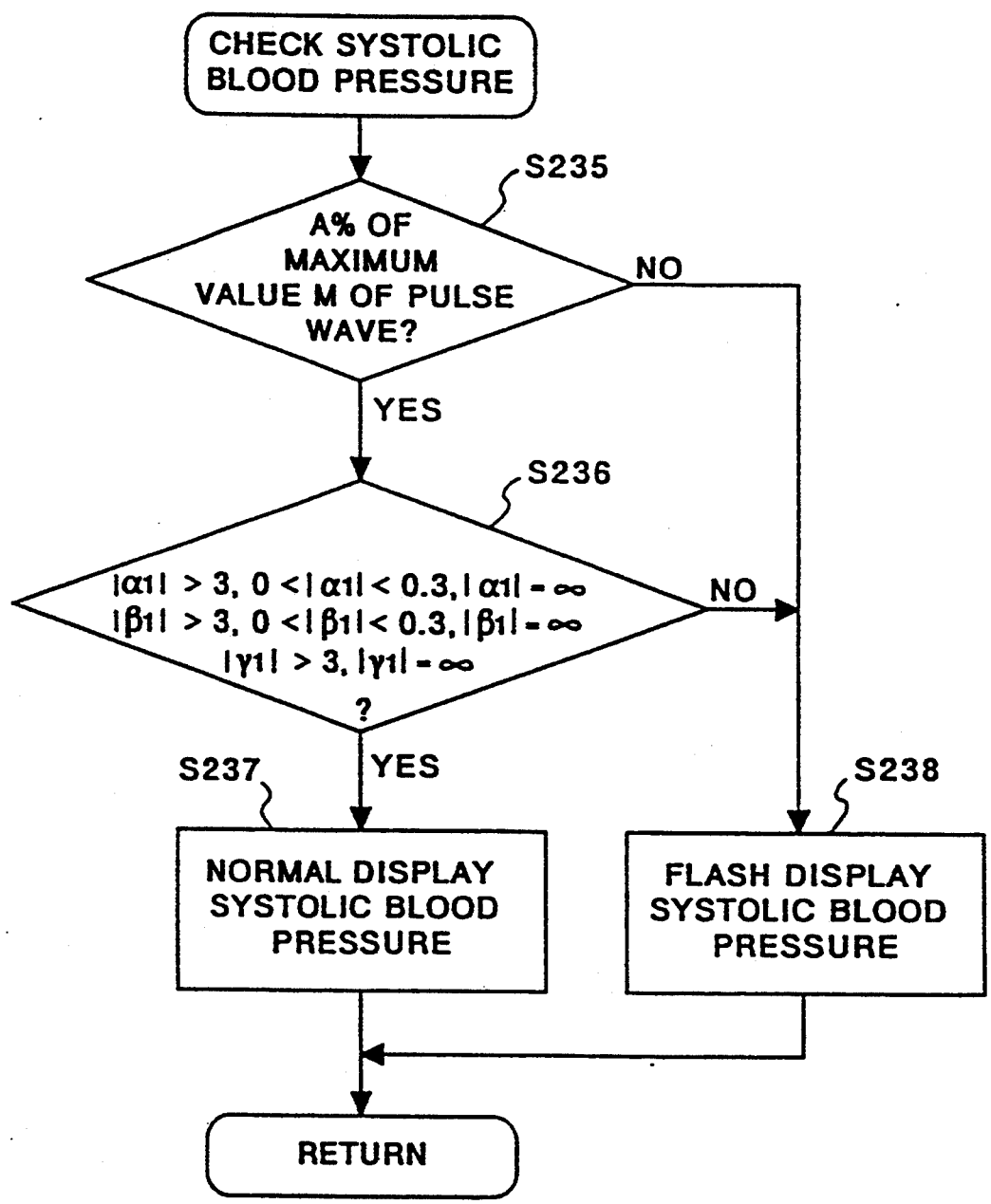
F I G. 12B

ELECTRONIC SPHYGMOMANOMETER

This is a division of application Ser. No. 07/800,073 filed Nov. 27, 1991, now U.S. Pat. No. 5,218,967, which is a Divisional application of Ser. No. 07/591,410, filed Oct. 10, 1990 (now U.S. Pat. No. 5,103,830).

BACKGROUND OF THE INVENTION

1. Field of the Invention

The present invention relates to an electronic sphygmomanometer, and, more particularly, to an electronic sphygmomanometer arranged to be operated in accordance with the Korotkoff method and the oscillometric method.

2. Description of the Prior Art

In a blood pressure measuring method performed without watching blood, systolic blood pressure, diastolic blood pressure and mean blood pressure are measured based on a change of blood flow in an artery under a cuff which is wrapped on a blood pressure measuring portion, through a process of reducing the pressure of the cuff at a slow fixed speed after the pressurization of the cuff over expected systolic blood pressure through a process of pressuring the cuff at a fixed speed from a pressure less than the diastolic blood pressure to a pressure more than the systolic blood pressure. Such methods include he Riva-Rocci-Korotkoff method of measuring the blood pressure in accordance with a recognition of Korotkoff sounds (to be called the "K-sound method" hereinafter) and the oscillometric method of measuring the blood pressure in accordance with the oscillating pulse wave overlapping on the cuff pressure (to be called the "OSC method" hereinafter).

Conventional electronic sphygmomanometers have been arranged to act in accordance with only either method of the above-described methods: the K-sound method and the OSC method. Therefore, these electronic sphygmomanometers have included the advantages and the drawbacks of each method. For example, a problem arises in that an accurate blood pressure level cannot be obtained from persons who show too weak a K-sound to be detected, from persons having strong pulses and from patients who are being subjected to artificial dialysis and who therefore show strong artery shunt noise, causing the K-sound to be undesirably detected to a level below the diastolic blood pressure. On the other hand, the OSC method sphygmomanometer has a problem in that the blood pressure cannot be accurately measured from a person who shows too small oscillating pulse waves, when the cuff belt is wound too loosely, when a relatively large cuff is wound around a thin arm or when the blood pressure change is too excessive during the blood pressure measurement operation (the blood pressure change at breathing time).

SUMMARY OF THE INVENTION

Accordingly, an object of the present invention is to overcome the above-described problems experienced with the conventional electronic sphygmomanometers by providing an electronic sphygmomanometer capable of overcoming the conventional problem which cause blood pressure to be improperly measured, which electronic sphygmomanometer displays an accurate blood pressure level by making good use of the advantages of both the K-sound and OSC methods and avoiding the drawback of each.

Another object of the present invention is to provide an electronic sphygmomanometer capable of accurately determining that the oscillation in cuff pressure is too small and eliminating an error from the result of the measurement of the blood pressure which has taken place due to the fact that the oscillation in cuff pressure is small.

A further object of the present invention is to provide an electronic sphygmomanometer capable of accurately determining that the oscillation in cuff pressure is too small, eliminating an error from the result of the measurement of the blood pressure which has taken place due to the fact that the oscillation in cuff pressure is small and eliminating an error from the result of the measurement of the diastolic blood pressure due to a change caused from slight and sole arhythmia and respiration.

A still further object of the present invention is to provide a reliable electronic sphygmomanometer which because of its structure is arranged in such a manner that probable checking is performed.

Another object of the present invention is to provide a reliable electronic sphygmomanometer in which the probable checking is performed by obtaining the blood pressure levels at the time of pressure application and pressure reduction.

In order to achieve the above-described objects, according to the present invention, an electronic sphygmomanometer is disclosed which is arranged to act depending upon both the Korotkoff method and the oscillometric method and capable of accurately measuring the blood pressure and overcoming the problems taken place in that the blood pressure cannot be measured, the above-described effects being obtainable according to the two advantages of the above-described two methods.

An aspect of the present invention lies in an electronic sphygmomanometer comprising: first blood pressure measuring means for measuring the blood pressure at the time of reducing the cuff pressure in accordance with the generation or the disappearance of Korotkoff sound; second blood pressure measuring means for measuring the blood pressure at the time of reducing the cuff pressure in accordance with a oscillating pulse wave signal of the cuff; and blood pressure selection means for selecting and displaying the result of the measurement performed by the first blood pressure measuring means and the second blood pressure measuring means corresponding to the relationships between the timing at which the Korotkoff sound is generated, the timing at which the same disappears and the timing at which the blood pressure is detected in accordance with the oscillating pulse wave.

In the case of measuring the blood pressure of one whose Korotkoff sound is difficult to be detected, when no Korotkoff sound more than predetermined level has been detected by the first blood pressure measuring means not later than the detection of a mean blood pressure by the second blood pressure measuring means, the blood pressure selection means selects the systolic blood pressure and the diastolic blood pressure measured by the second blood pressure measuring means, while, in the case where the Korotkoff sound has been detected not later than the mean blood pressure is detected, the blood pressure selection means selects the systolic blood pressure measured by the first blood pressure measuring means.

In the case where the Korotkoff sound has been detected at a pressure level of {mean blood pressure−(systolic blood pressure−mean blood pressure)} or less, the blood pressure selection means selects the diastolic blood pressure measured by the second blood pressure measuring means, while, in the case where the Korotkoff sound disappears at the pressure level of {mean blood pressure−(systolic blood pressure−mean blood pressure)} or more, the diastolic blood pressure measured by the first blood pressure measuring means is selected.

In the case where the Korotkoff sound has been detected after the pressure level had been reduced by about 15 mmHg after recognition of the diastolic blood pressure by the second blood pressure measuring means, the blood pressure selection means selects the diastolic blood pressure measured by the second blood pressure measuring means, while, in the case where the Korotkoff sound disappears not later than the reduction of the pressure by about 15 mmHg, the diastolic blood pressure measured by the first blood pressure measuring means is selected.

An electronic sphygmomanometer according to the present invention comprises display means or instruction means for displaying or instructing the result of the measurement performed by the first blood pressure measuring means of the result of the measurement performed by the second blood pressure measuring means.

According to the above-described structure, both the measurement of the blood pressure in accordance with the OSC method and that in accordance with the K-sound method are performed so that either of the above-described blood pressure levels is selectively displayed in accordance with the relationship between the time at which the Korotkoff sound has been generated and the time at which the predetermined blood pressure level has been detected in accordance with the above-described oscillating pulse wave. Therefore, even if the blood pressure cannot be measured by either of the K-sound method or the OSC method, the blood pressure can be measured. In addition, the reliability of the result of the measurement can be confirmed by an operator since the subject result of the measurement of the blood pressure is obtained in accordance with either the K-sound method or the OSC method. Furthermore, since either of the blood pressure levels respectively obtained in accordance with the K-sound method and the OSC method is displayed in response to an instruction, the blood pressure levels respectively obtained from the K-sound method and the OSC method can be subjected to a comparison with each other. Therefore, a problem arisen in that the blood pressure cannot be measured can be overcome and an accurate blood pressure level can thereby be displayed.

Another aspect of the present invention lies in an electronic sphygmomanometer acting in accordance with both a Korotkoff method in which blood pressure is measured in accordance with the generation or disappearance of Korotkoff sound by pressing a portion of the human body and an oscillometric method in which the blood pressure is measured in accordance with the change in the level of oscillation in cuff pressure overlapping the pressure of the cuff and due to the time phase, the electronic sphygmomanometer comprising oscillation in cuff pressure measurement stopping means for stopping the measurement of the oscillation in cuff pressure in accordance with a detection of the oscillation in cuff pressure not later than the recognition of the systolic blood pressure or the diastolic blood pressure obtained in accordance with the Korotkoff method.

The above-described oscillation in cuff pressure measurement stopping means stops the measurement of the oscillation in cuff pressure in the case where the oscillation in cuff pressure corresponding to the Korotkoff sound which has been first detected is less than a predetermined number of pulses.

According to the present invention, an electronic sphygmomanometer has a cuff which is arranged to be placed on a body part of a person. A first time zone determining means determines a first time zone, in which Korotkoff sound is expected to occur, in accordance with a cuff pressure oscillation during a depressurizing of the cuff; and blood pressure recognizing means recognizes a blood pressure in accordance with a generation of Korotkoff sound in the first time zone determined by the first time zone determining means. A time zone determination stopping means is provided for stopping the determination of the first time zone performed by first time zone determining means when a condition of detected cuff pressure oscillations, before a recognition point of a systolic blood pressure, meets a predetermined condition.

According to another feature of the present invention, the time zone determination stopping means includes means for stopping the determination of the first time zone when a number of cuff pressure oscillations detected before a detection of a first Korotkoff sound is less than a predetermined number of cuff pressure oscillations.

According to a further feature of the present invention, a second time zone determining means is provided for determining a second time zone having a predetermined time width, in which a next Korotkoff sound is expected to occur, after a recognition point of a present Korotkoff sound; and in a case where the determination of the first time zone is stopped by the time zone determination stopping means, the blood pressure recognizing means recognizes a blood pressure by using the second time zone by the second time zone determining means.

According to the above-described structure, the fact that the oscillation in cuff pressure is too small can be accurately determined and the error in the measurement of the blood pressure taken place due to the fact that the oscillation in cuff pressure is too small can be eliminated by using the oscillation in cuff pressure as the gate for the Korotkoff sound and by making a determination whether or not the oscillometric method is executed at the time when the systolic blood pressure is recognized.

Furthermore, since the means for setting a time zone for recognizing the next Korotkoff sound of a predetermined time width for each recognition of the Korotkoff sound is provided, the noise in the detection in accordance with only the Korotkoff sound is discriminated and the error from the result of the measurement of the diastolic blood pressure due to the change caused from slight and sole arhythmia and respiration can be eliminated.

Still another aspect of the present invention lies in an electronic sphygmomanometer for measuring blood pressure by pressing a portion of the human body, comprising: point detection means for detecting a point of the systolic blood pressure and that of the diastolic blood pressure in accordance with the generation or the disappearance of Korotkoff sound; determining means for determining the validity of the points in accordance with the height of the oscillating pulse wave at the point and the change in the height of the oscillating pulse wave in the vicinity of the point; and display means for displaying the blood pressure in accordance with the result of the determination made by the determining means.

The point detection means detects each of the points at the time of pressure application and reduction so as to determine the validity of the point in accordance with the blood pressure level obtained at the time of the pressure application and the blood pressure level at the time of the pressure reduction.

According to the above-described structure, a phenomenon that the capacity of the blood vessel under the cuff is changed at the times when the Korotkoff sound is generated and allowed to disappear is utilized so that the validity of the systolic and the diastolic blood pressures recognized in accordance with the Korotkoff method can be determined with a probability in a certain range, causing the reliability of the result of the measurement of the blood pressure to be improved.

Other and further objects, features and advantages of the invention will be appear more fully from the following description.

BRIEF DESCRIPTION OF THE DRAWINGS

FIG. 5 is a block diagram which illustrates an essential portion of a second embodiment of the electronic sphygmomanometer according to the present invention;

FIGS. 12A and 12B are flow charts which illustrate the checking routine of the systolic blood pressure according to the example shown in FIG. 10;

DETAILED DESCRIPTION

Figure 1A:
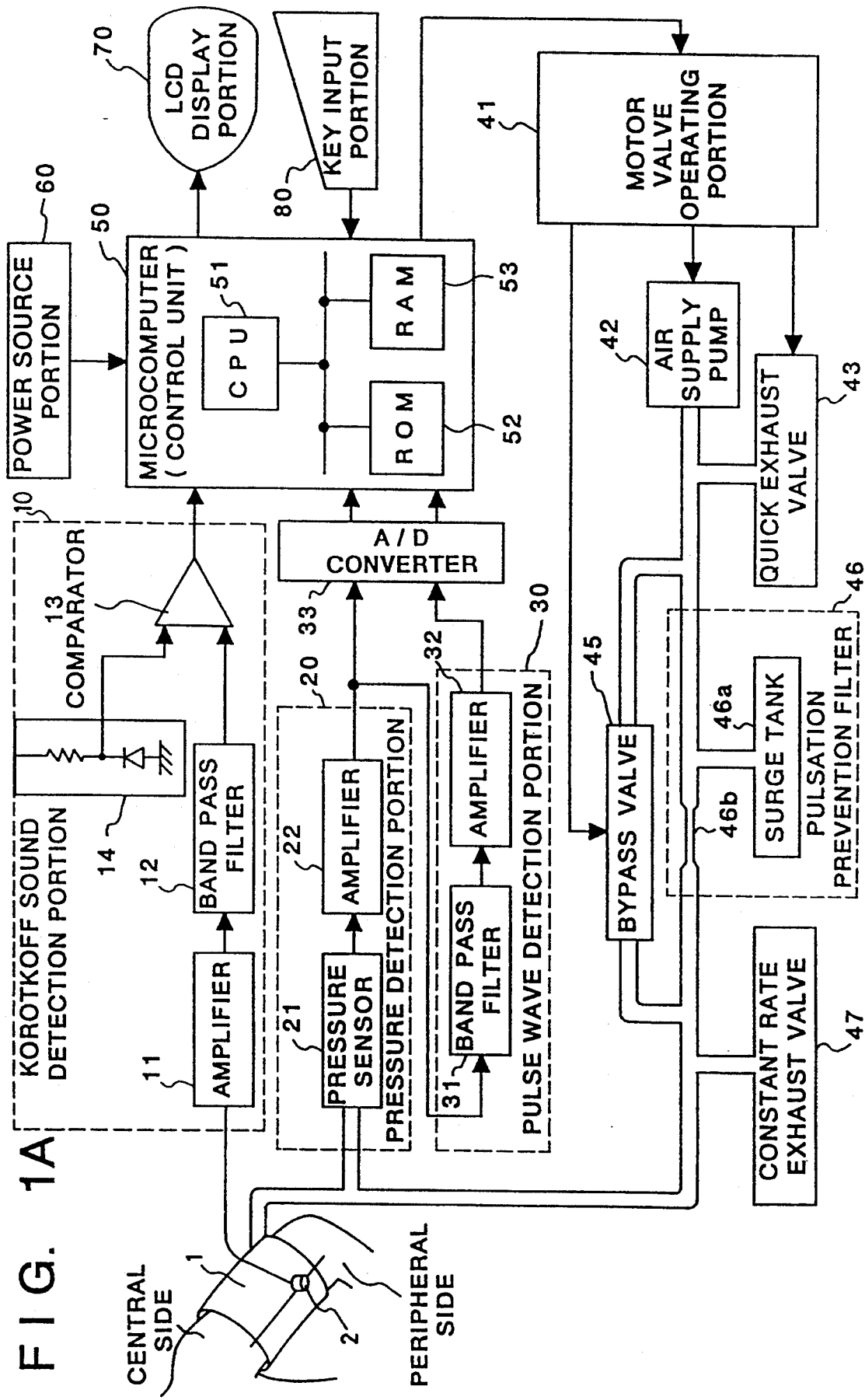
FIG. 1A is a block diagram which illustrates the structure of an electronic sphygmomanometer according to the present invention.

FIG. 1A is a block diagram which illustrates the structure of an embodiment of an electronic sphygmomanometer according to the present invention.

The sphygmomanometer according to the present invention comprises a cuff 1 pressing a portion of a human body and a Korotkoff sound sensor 2 disposed in the periphery of the cuff 1. A signal transmitted from the Korotkoff sound sensor 2 is supplied to a Korotkoff sound detection portion 10. The signal is amplified by an amplifier 11, and then the signal thus amplified is passed through a band pass filter 12 and supplied to a comparator 13 which determines that there are Korotkoff sounds if the level of the above-described signal exceeds a certain threshold value supplied from a threshold value input circuit 14. The signal denoting that the Korotkoff signal has been confirmed is supplied to a microcomputer 50.

On the other hand, a signal transmitted from a pressure sensor 21 connected to the cuff 1 is supplied to a pressure detection portion 20. Then, the signal thus received is amplified by an amplifier 22 before it is supplied to an A/D converter 33 so that a digital signal formed by the A/D converter 33 is supplied to the microcomputer 50. A signal transmitted from the pressure sensor 21 is amplified by an amplifier 22 before it is supplied to a oscillating pulse wave detection portion 30. Then, it passes a band pass filter 31 for restricting the frequency band for the purpose of eliminating a DC component and cancelling noise. Then, the signal is amplified by an amplifier 32 before the signal is supplied to the A/D converter 33 so that a digital output is obtained which is then supplied to the microcomputer 50.

The microcomputer 50 (to be also called a "control unit" hereinafter) comprises a CPU 51 acting to calculate data and controlling the overall system, a ROM 52 for storing a control program and a RAM 53 serving as a sub-storage means. The microcomputer 50 is operated by power supplied from a power source 60 so that it detects the generation or disappearance of the Korotkoff sounds in accordance with the Korotkoff sound recognition signal supplied from the Korotkoff sound detection portion 10. The microcomputer 50 also acts to recognize the blood pressure in accordance with data denoting the height of the oscillating pulse wave or the area of the same supplied from the oscillating pulse wave detection portion 30 in addition to a function of checking the points at which the Korotkoff sounds have been respectively generated and the same have disappeared. Furthermore, the microcomputer 50 causes an LCD display portion 70 to display, as the level of the blood pressure, the cuff pressures at the generation and disappearance points of the Korotkoff sounds or the blood pressure recognition point. Furthermore, the microcomputer 50 is provided with a key input portion 80 through which the power supply can be instructed.

The microcomputer 50 operates an air supply pump 42, a quick exhaust valve 43 and a bypass valve 45 via a motor operating portion 41 so that the pressure in the cuff 1 is controlled. A pulsation prevention filter 46 comprising a surge tank 46a and a fluid resistor 46b is disposed between the cuff 1 and the air supply pump 42. The microcomputer 50 controls the above-described pumps and the valves by observing the cuff pressure so as to realize a desired cuff pressure level. Reference numeral 47 represents a constant rate exhaust valve acting at the time when the pressure is lowered.

Figure 1B:
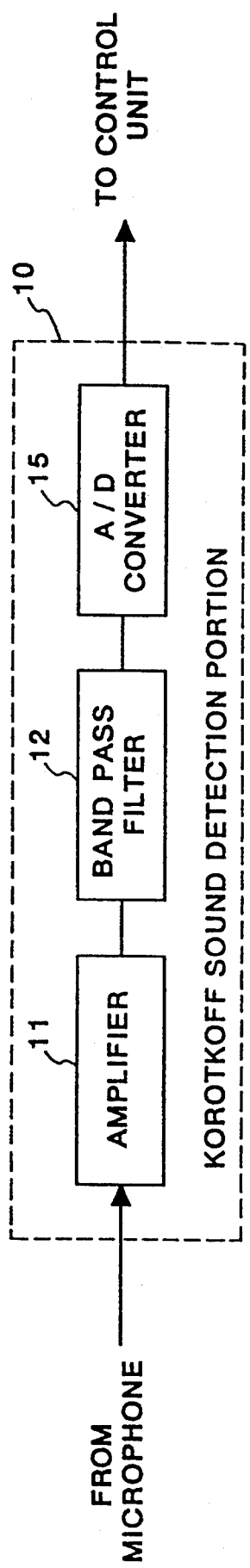
FIG. 1B illustrates another structure of the Korotkoff sound detection portion 10 shown in FIG. 1A.

FIG. 1B illustrates another example of the structure of the Korotkoff sound (K-sound) detection portion 10. In this case, the Korotkoff sounds can be recognized from the waveform.

The Korotkoff sound detection portion 10 comprises a microphone 11 for sensing the blood flow, an amplifier 12 for amplifying the output voltage from the microphone 11, a band pass filter 13 for filtering a predetermined band which corresponds to the Korotkoff sound and an A/D converter 14. It is preferable that the amplifier 12 is arranged to be a type which is able to amplify the predetermined band.

First Embodiment

Figure 2:
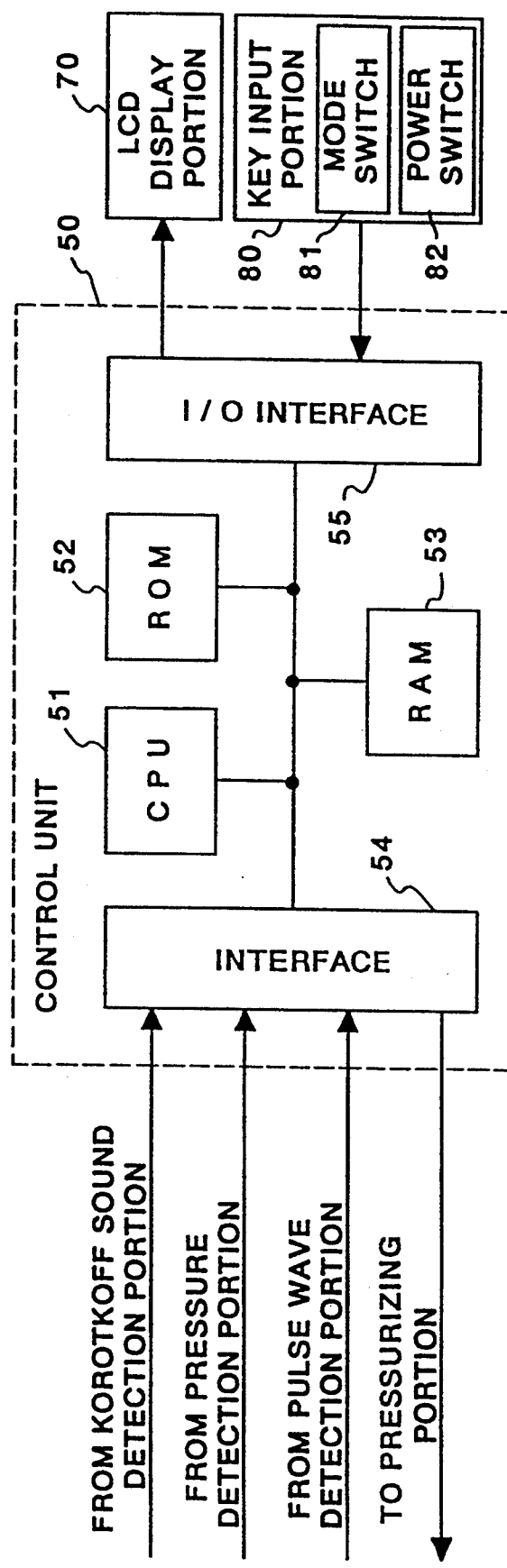
FIG. 2 is a block diagram which illustrates an essential portion of a first embodiment of an electronic sphygmomanometer according to the present invention.

FIG. 2 is a block diagram which illustrates an essential Portion of an electronic sphygmomanometer according to a first embodiment of the present invention.

The control unit 50 comprises the CPU 51, the ROM 52 for storing the control program for the CPU 51, the RAM 53 serving as a sub-storage means and acting to store supplied data, and I/O interfaces 54 and 55. Reference numeral 70 represents the display of the liquid crystal type or the like for displaying the result of the measurement and reference numeral 80 represents the key input portion through which an instruction of an operator is inputted, the key input portion 80 having a mode switch capable of switching the measurement mode and a power switch 82.

Figure 3:
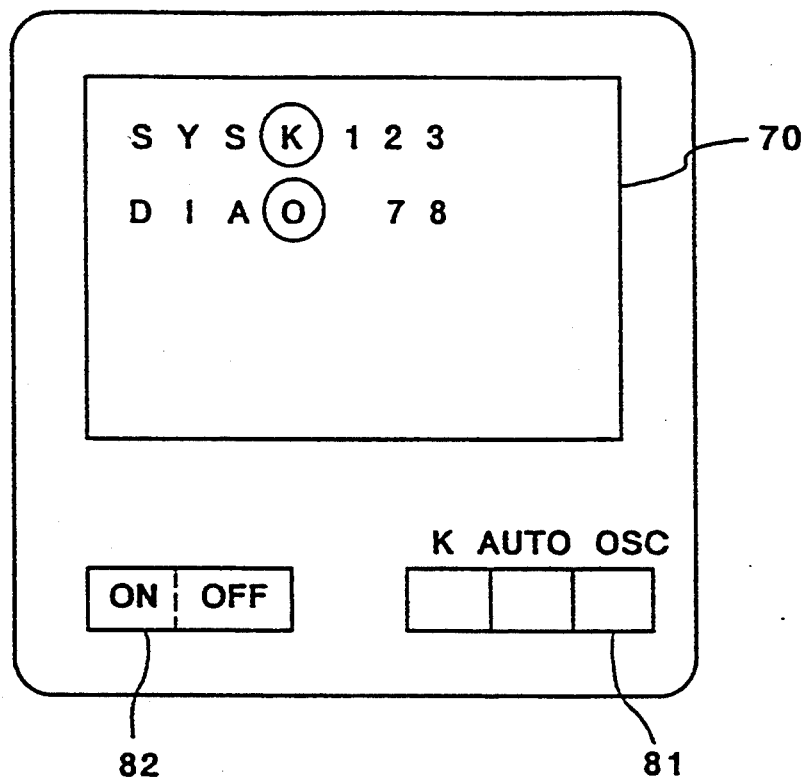
FIG. 3 illustrates an example of a display performed by the electronic sphygmomanometer according to the first embodiment of the present invention.

FIG. 3 illustrates the shape of the sphygmomanometer according to the first embodiment of the present invention.

Figure 4A:
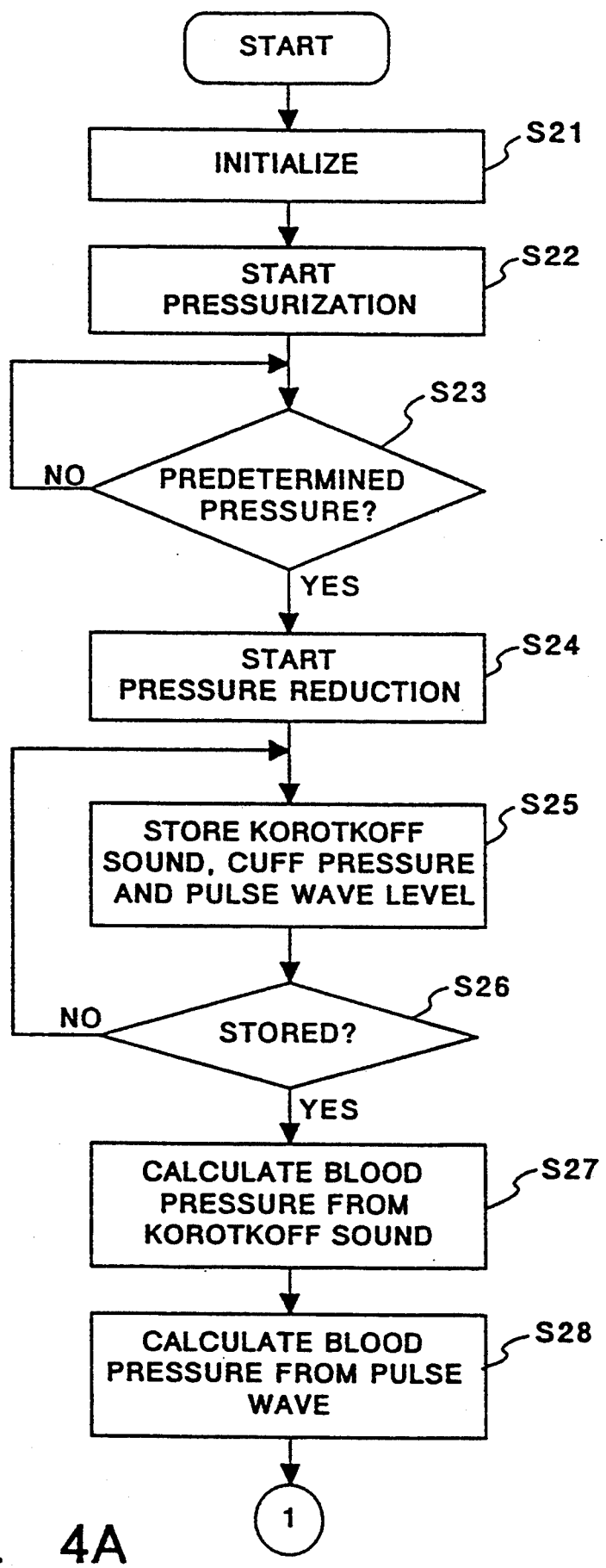
FIG. 4 is a flow chart which illustrates the flow of the measurement operation performed by the electronic sphygmomanometer according to the first embodiment of the present invention.
Figure 4B:
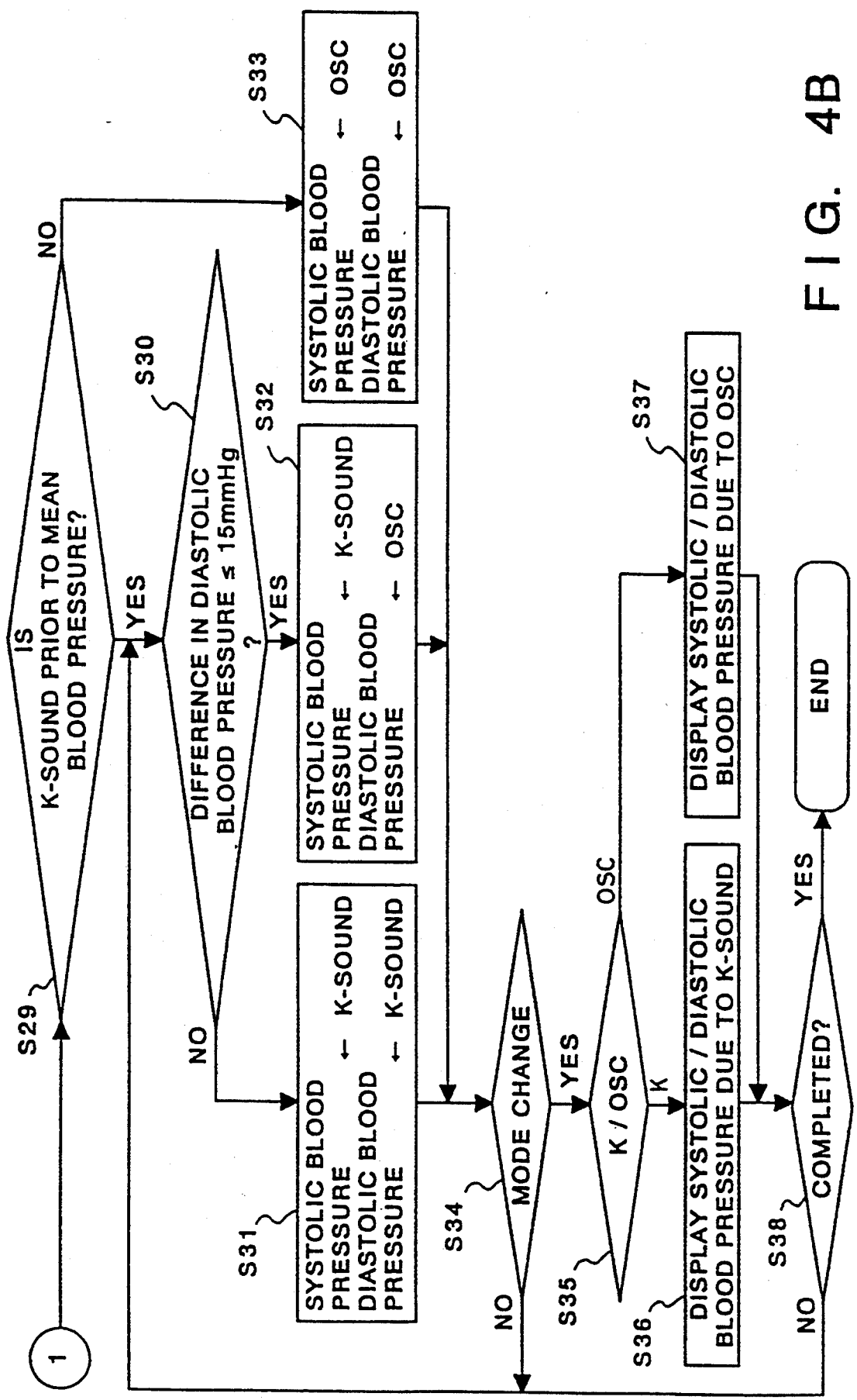

FIG. 4 is a flow chart which illustrates the measurement operation performed by the sphygmomanometer according to the first embodiment of the present invention.

After the power has been turned on, the sphygmomanometer is initialized in step S21 in which, for example, the cuff pressure is set to zero. In step S22, the pressure application to the cuff 1 is started. Then, the pressure is raised to a predetermined level (a level higher than the systolic blood pressure) in step S23, and the pressure reduction is started in step S24. At the time during the above-described pressure reduction process, the Korotkoff sound supplied from the Korotkoff sound measuring portion 10, the cuff pressure and the height of the oscillating pulse wave supplied from the cuff pressure/oscillating pulse wave measuring portion 20 are stored in the RAM 33 in step S25 in such a manner that the Korotkoff sound and the cuff pressure and the height of the oscillating pulse wave are made to correspond to the time at which the measurement is made. In step S26, the completion of the data collection, for example, the time at which the peak-to-peak values successively become lower than a predetermined threshold value for five pulses is waited for, the peak-to-peak value being obtained from (the maximum value — the minimum value), where the maximum and the minimum values are those of a signal supplied from the Korotkoff sound measuring portion 10 detected at each generation of the pulses. If the above-described condition is satisfied, the data collection is stopped and the flow advances to step S27.

In step S27, the systolic and diastolic blood pressures are respectively calculated in accordance with the Korotkoff sounds. For example, the calculation is made in such a manner that the first cuff pressure after the Korotkoff sounds have been successively generated two times is defined as the systolic blood pressure and the first cuff pressure after the Korotkoff sounds have successively disappeared three times is defined as the diastolic blood pressure.

In step S28, the systolic blood pressure, the mean blood pressure and the diastolic blood pressure are calculated in accordance with the oscillating pulse wave. For example, the calculation is made in such a manner that the level corresponding to the time at which the height of the oscillating pulse wave becomes its maximum value is defined as the mean blood pressure, the level corresponding to the time at which the height of the oscillating pulse wave exceeds 40% of the maximum height of the oscillating pulse wave is defined as the systolic blood pressure and the level corresponding to the time at which the height of the pulse wave exceeds 70% of the maximum height of the oscillating pulse wave is defined as the diastolic blood pressure.

In accordance with the value calculated in steps S27 and S28, it is, in step S29, determined whether or not the Korotkoff sound had been detected prior to the time at which the mean blood pressure has been observed. If the Korotkoff sound had been detected immediately after the mean blood pressure, the flow advances to step S33 in which the value of each of the systolic blood pressure and the diastolic blood pressure calculated in accordance with the oscillating pulse wave is displayed. In the case where the Korotkoff sound can be detected even if the pressure has been lowered by a predetermined degree (about 15 mmHg according to this embodiment) after the diastolic blood pressure had been recognized in accordance with the presence of the Korotkoff sound, the flow advances from S29 to S32 via S30 so that the value of the systolic blood pressure calculated in accordance with the Korotkoff sound and the value of the diastolic blood pressure calculated in accordance with the oscillating pulse wave are displayed.

The above-described predetermined pressure can be calculated from the following equation:

$$\{(\text{Mean blood pressure} - (\text{Systolic blood pressure} - \text{Mean blood pressure})\}$$

The average value of the above-described blood pressure usually becomes about 15 mmHg according to statistical analysis. However, the present invention is not limited to the above-described value and another value may be selected also in the description made hereinafter.

In the case where the Korotkoff sounds disappear when the pressure does not drop by about 15 mmHg after the diastolic blood pressure has been recognized in accordance with the oscillating pulse wave, the flow advances from S29 to S31 via S30 so that the values of the systolic and diastolic blood pressures calculated in accordance with the Korotkoff sound are displayed. In order to indicate the fact that the value displayed is recognized in accordance with the Korotkoff sound or the oscillating pulse wave, symbol k is displayed in the case of the Korotkoff sound while symbol o is displayed in the case of the oscillating pulse wave.

In step S34, the mode of a mode switch 81 is detected, the mode being arranged to be selectable between a mode in which the value calculated in accordance with the Korotkoff sound is displayed and a mode in which the value calculated in accordance with the oscillating pulse wave is displayed. If the instructed mode is the mode (side K shown in FIG. 3) in which the value calculated in accordance with the Korotkoff sound is displayed, the flow advances from step S34 to S36 via S35 so that the value calculated in accordance with the Korotkoff sound is displayed regardless of the above-described condition. In step S38, whether or not the display operation has been completed (or cleared) is detected. If the operation has not been completed, the flow returns to step S30 in which the display operation is again performed.

According to this embodiment, the result of the measurement according to the OSC method is displayed depending upon the result of a determination made about the reliability of the result of the measurement made in accordance with the K-sound method. However, another method in which the result of the measurement calculated in accordance with the K-sound method is displayed in the case where the height of the wave calculated in accordance with the OSC method is smaller than the predetermined threshold value is, of course, included within the scope of the invention.

According to this method, an electronic sphygmomanometer, capable of overcoming the problem that the measurement cannot be performed and thereby displaying an accurate blood pressure, can be provided.

The case where no K-sound is detected prior to the time at which the mean blood pressure has been calculated in accordance with the OSC method, the measurement of the blood pressure in accordance with the K-sound method cannot be easily performed. A further accurate measurement of the blood pressure can be performed by displaying the blood pressure detected in accordance with the OSC method by cancelling the display of the inaccurate blood pressure obtained in accordance with the K-sound method. Furthermore, the necessity of again performing the measurement of the blood pressure can be eliminated. The phenomenon, in which K-sounds are detected even after the blood pressure has been dropped by about 15 mmHg after the diastolic blood pressure had been confirmed in accordance with the OCS method, is frequently observed from the measurement of a person in an exasperation state, a person showing extremely strong pulses or a person taking dialysis treatment and showing large artery shunt sounds. In this case, the diastolic blood pressure calculated in accordance with the OSC method is approximated to the natural blood pressure. Therefore, a further accurate measurement of the blood pressure can be performed by displaying the diastolic blood pressure calculated in accordance with the OSC method.

Usually the blood pressure levels, which are respectively measured in accordance with the K-sound method and the OSC method, do not coincide with each other since they are arranged to measure the blood pressure level in different ways. Since the method, either the OSC method or the K-sound method, which has been employed to detect the blood pressure level, is displayed, and the systolic blood pressure and the diastolic blood pressure detected in accordance with each of the K-sound method and the OSC method are displayed in response to an external command, the blood pressure level measuring method suitable for each person can be employed.

Second Embodiment

In the second embodiment, the blood pressure is recognized based on the Korotkoff sound within a pulse wave gate which is generated in accordance with each of the cuff pressure oscillations. When the level of the cuff pressure oscillations is low, the pulse wave gate is not used to prevent the sphygmomanometer from causing errors. In this second embodiment, both the pulse wave gate and a time width gate having a predetermined time width after detecting a present Korotkoff sound are generated, and then the time width gate is used to prevent the sphygmomanometer from causing an error when the level of the cuff pressure oscillations is low.

FIG. 5 is a block diagram which illustrates an essential portion of a second embodiment of the electronic sphygmomanometer according to the present invention.

Figure 7:
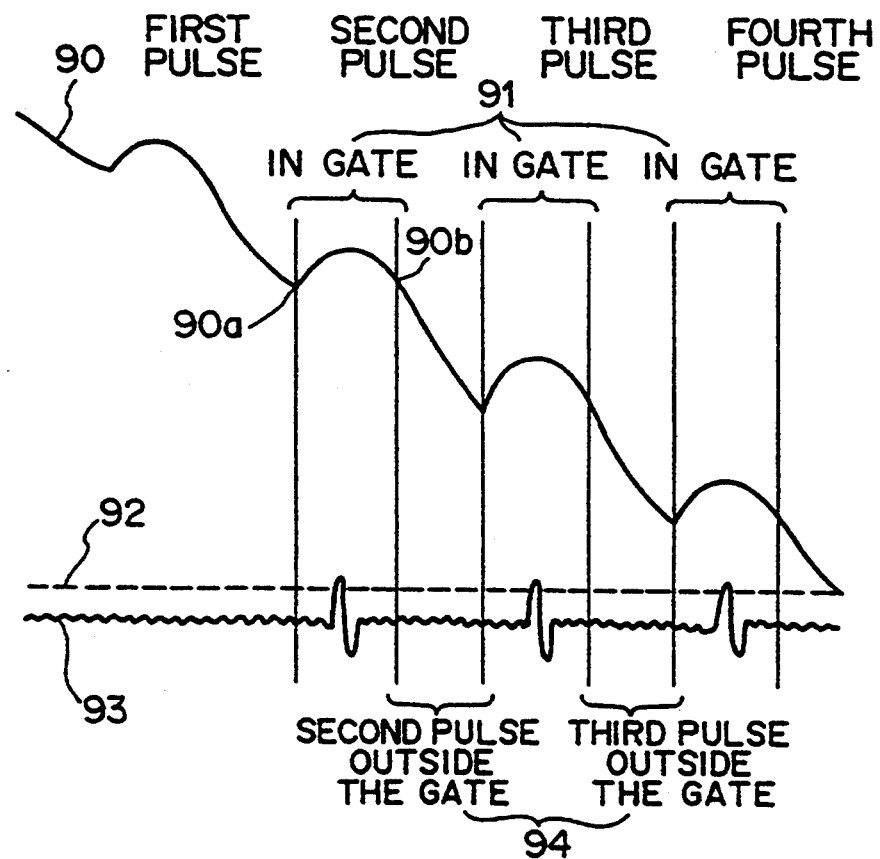
FIG. 7 illustrates output signals from the respective blocks of the electronic sphygmomanometer according to the second embodiment of the present invention.

FIG. 7 illustrates output signals corresponding to the respective blocks.

Reference numeral 90 represents output data from the pressure detection portion 20 and reference numeral 93 represents output data from the Korotkoff sound detection portion 10.

The control unit 50 recognizes the systolic blood pressure and the diastolic blood pressure denoted by output data 93 supplied from the Korotkoff sound detection portion 10 in accordance with a thresh level 92 processed in a gate 91 in accordance with the output data 90 supplied from the pressure detection portion 20. The above-described control portion 50 comprises the CPU 51 for calculating data and controlling the system, the ROM 52 for storing the control program for the CPU 51, the RAM 53 serving as sub-storage means and acting to store supplied data and I/O interfaces 54 and 55. The CPU 51 has flags $S_1$, $S_2$, $D_1$ and $D_2$ ($51a$ to $51d$), while the RAM 53 has storage means $SYS_1$ for storing the systolic blood pressure calculated in accordance with the oscillating pulse wave gate, $DIA_1$ for storing the diastolic blood pressure, $SYS_2$ for storing the systolic blood pressure in accordance with the time width and calculated in accordance with the previous Korotkoff sound and $DIA_2$ for storing the diastolic blood pressure ($53a$ to $53d$). Reference numeral 70 represents the display and 80 represents the key input portion through which an instruction of an operator is inputted, the key input portion 80 having a power source switch 52 and the like.

In response to the pressure signal 90 supplied from the pressure sensor 21 and converted into a digital value by the A/D converting portion 33, a gate 91 is formed to recognize the Korotkoff sound by using a minimal point $90a$ and a next point $90b$ of the same level. In the thus processed gate 91, a comparison between the digital signal supplied from the microphone 2 via the A/D conversion portion 15 and a predetermined threshold level 92 is made so that the Korotkoff sound is extracted. On the other hand, noise is extracted as a result of a comparison made with the predetermined threshold level 92. Then, the level (the peak and the bottom) of the sound is measured in response to the digital signal supplied from the Korotkoff sound detection portion 10. As a result, a recognition that there is a Korotkoff signal is made in the case where the level thus obtained exceeds a certain level and simultaneously the sound is within the gate, which is made from the oscillation in cuff pressure overlapping the digital signal supplied from the pressure detection portion.

On the other hand, the cuff pressure level at the timing of the Korotkoff sound which has been first detected after, for example, two Korotkoff sounds have been successively detected is recognized as the systolic blood pressure. Simultaneously with the above-described operation for recognizing the systolic blood pressure, the Korotkoff sound recognition operation is performed in which the following conditions are the recognition conditions of the systolic blood pressure: the level of the digital signal supplied from the Korotkoff sound detection portion has exceeded a certain threshold value and each of the intervals of, for example, three pulses of the signal is ranged in 0.35 to 2 seconds.

In the case where the systolic blood pressure is recognized since the above-described former conditions have not met, if the cuff pressure level at the timing of the systolic blood pressure has dropped by 30 mmHg or more from the start of the pressure reduction and simultaneously the oscillation in cuff pressure at the timing of the systolic blood pressure is positioned at the position corresponding to three pulses or more from the time at which the oscillation in cuff pressure has been first recognized, the data obtained in accordance with the latter method is deleted to efficiently use the work area. Furthermore, the recognition in accordance with the Korotkoff sound is continued by using the gate processed in accordance with the oscillation in cuff pressure. As a result, the cuff pressure level, at the timing of the Korotkoff sound which is the last Korotkoff sound recognized when two pulses of the Korotkoff sounds are not successively recognized, is defined as the diastolic blood pressure.

When the systolic blood pressure is recognized, if the level of the cuff pressure, at the timing of the systolic blood pressure, has dropped by 30 mmHg or more from the start of the pressure reduction and the oscillation in cuff pressure is positioned within two pulses from the first detection of the oscillation in cuff pressure, it is determined that the level of the oscillating pulse wave is too low to rely on. Therefore, the operation of detecting the Korotkoff sound by using the oscillation in cuff pressure at the gate is stopped. In addition, the above-described detection operation in which only the Korotkoff sound is used is continued. In this case, an operation of retrieving the systolic blood pressure retroactive to the Korotkoff sounds which have been previously detected is performed so that the cuff pressure at the first timing when two pulses are successively detected is defined as the systolic blood pressure. However, if the pressure level at that timing has not dropped by 30 mmHg or more from the start of the reduction of the cuff pressure, the measurement of the systolic blood pressure is not performed but a notification as "pressure level insufficient" is made and only the recognition of the diastolic blood pressure is performed. In the case where no Korotkoff sound has been recognized for four seconds in the recognition operation of the Korotkoff sound performed continuously, the cuff pressure level at the timing of the final pulse is defined as the diastolic blood pressure.

In the case where no pulse wave has been recognized and the cuff pressure level has lowered to 30 mmHg or less, the blood pressure level is, of course, measured by the recognition method in accordance with only the Korotkoff sound.

The conditions for the gate in the case where the oscillating pulse wave gate is not used are set as follows. In the case where the continuity of the Korotkoff sounds is observed by using a sphygmomanometer for adults, a gate of an interval of the number of pulses (30 pulses/minutes to 200 pulses/minute), which are considered to be the ordinary number of pulses, that is, a gate of 0.35 seconds to 2 seconds from the previous Korotkoff sound is opened in accordance with the pulse which has been detected previously. Thus, the Korotkoff sound is detected in the gate thus opened. In the case where no Korotkoff sound is detected for four seconds which is twice two seconds corresponding to 30 pulses/minute from the Korotkoff sound recognized finally, it is determined as the "Fifth Point of Swan" (the Korotkoff sound disappearance sound). As a result, the cuff pressure level at that time is recognized as the diastolic blood pressure.

FIGS. 8A to 8D are flow charts which respectively illustrate the operation performed by the sphygmomanometer according to this embodiment.

In step S131, the sphygmomanometerometer is initialized after the power supply has been started, for example, Flags $S_1$, $S_2$, $D_1$ and $D_2$ are set to "0". In step S132, the pressure application is started, and the flow advances to step S133 in which the pressure rise up to a predetermined level is waited for. Then, the pressure reduction is started in step S134. In step S136, both the recognition of the Korotkoff sound in accordance with the oscillating pulse wave gate and the recognition of the same in accordance with the time width are performed as the pressure drops until a determination of flag $S_1$ or flag $S_2$ as "1" in step S137. The operations performed in steps S135 and S136 will be described later with reference to FIGS. 8C and 8D.

Figure 8A:
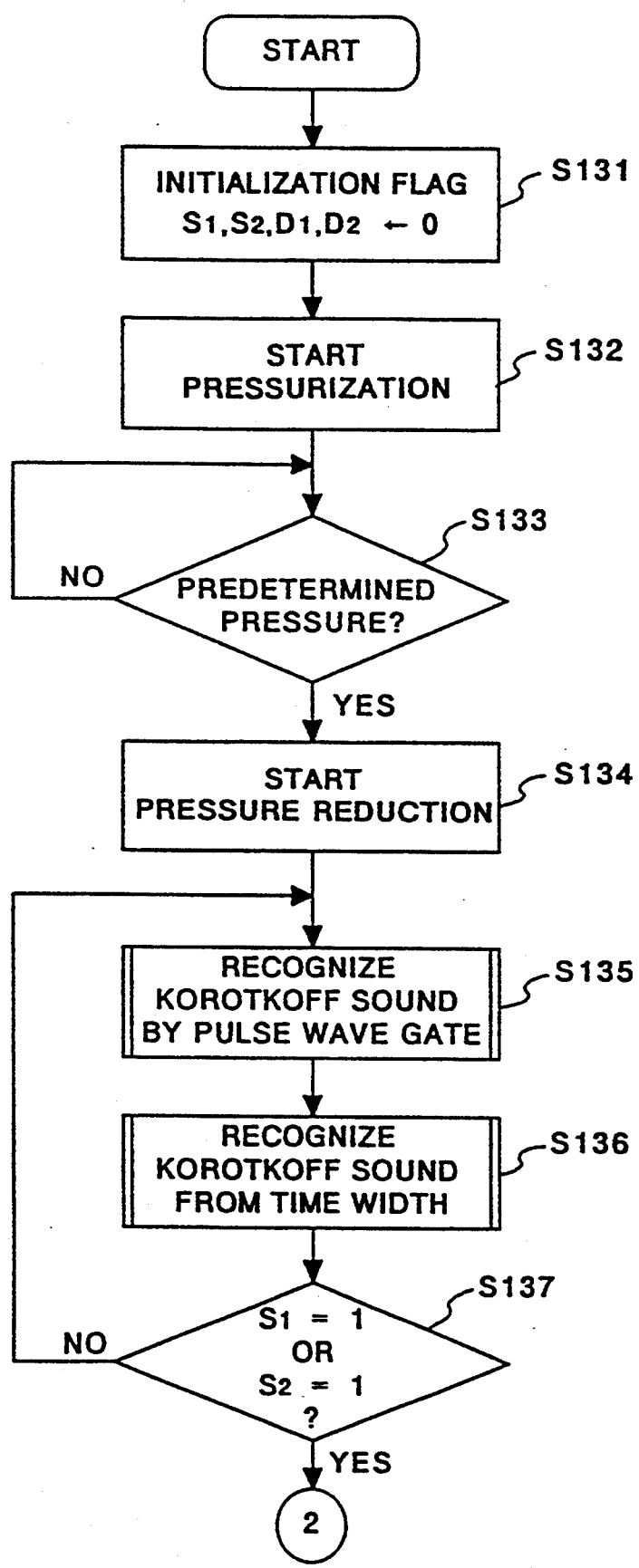
FIGS. 8A to 8D are flow charts which illustrate the flows of the operation of the electronic sphygmomanometer according to the present invention.
Figure 8B:
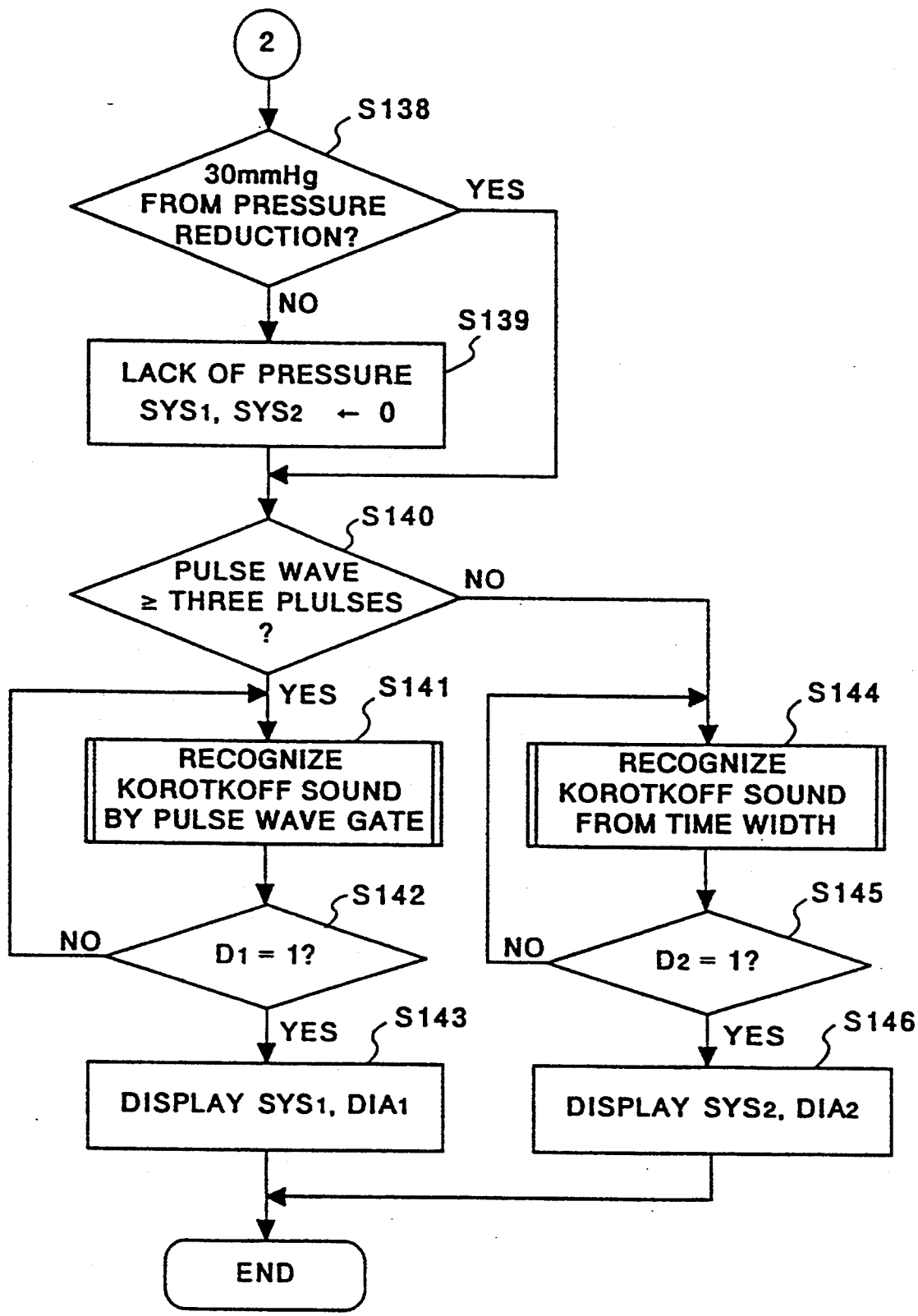

At the time when flag $S_1$ or $S_2$ becomes "1", that is, when the systolic blood pressure has been found, the flow advances from S137 to step S138 in as shown in FIG. 8B, it is determined whether or not the pressure has dropped by 30 mmHg or more from the start of the pressure reduction. If the pressure has not been dropped by the above-described degree, the flow advances to step S139 in which $SYS_1$ and $SYS_2$ are respectively set to "0" as a determination made as "pressure insufficient". If the pressure has been dropped by 30 mmHg or more, the flow advances to step S140 in which a determination is made whether or not there have been three pulses or more of the oscillation in cuff pressure until the systolic blood pressure is detected. If there have been three pulses or more, the flow advances to step S141 in which the recognition of the Korotkoff sound in accordance with the oscillating pulse wave gate is continued until flag $D_1$ becomes "1" in step S142, that is, the recognition of the diastolic blood pressure is waited for. Then, in step S143, the contents of $SYS_1$ and $DIA_1$ are displayed as the systolic blood pressure and the diastolic blood pressure.

If there have not been three pulses of the oscillation in cuff pressure until the detection of the systolic blood pressure, the flow advances from step S140 no step S144 in which the recognition of the Korotkoff sound in accordance with the oscillating pulse wave gate is stopped, but that in accordance with the time width is performed. In step S145, it is waited for that flag $D_2$ has become "1", that is, the recognition of the diastolic blood pressure is waited for. Then, in step S146, the contents of $SYS_2$ and $DIA_2$ are displayed as the systolic blood pressure and the diastolic blood pressure, respectively.

Figure 8C:
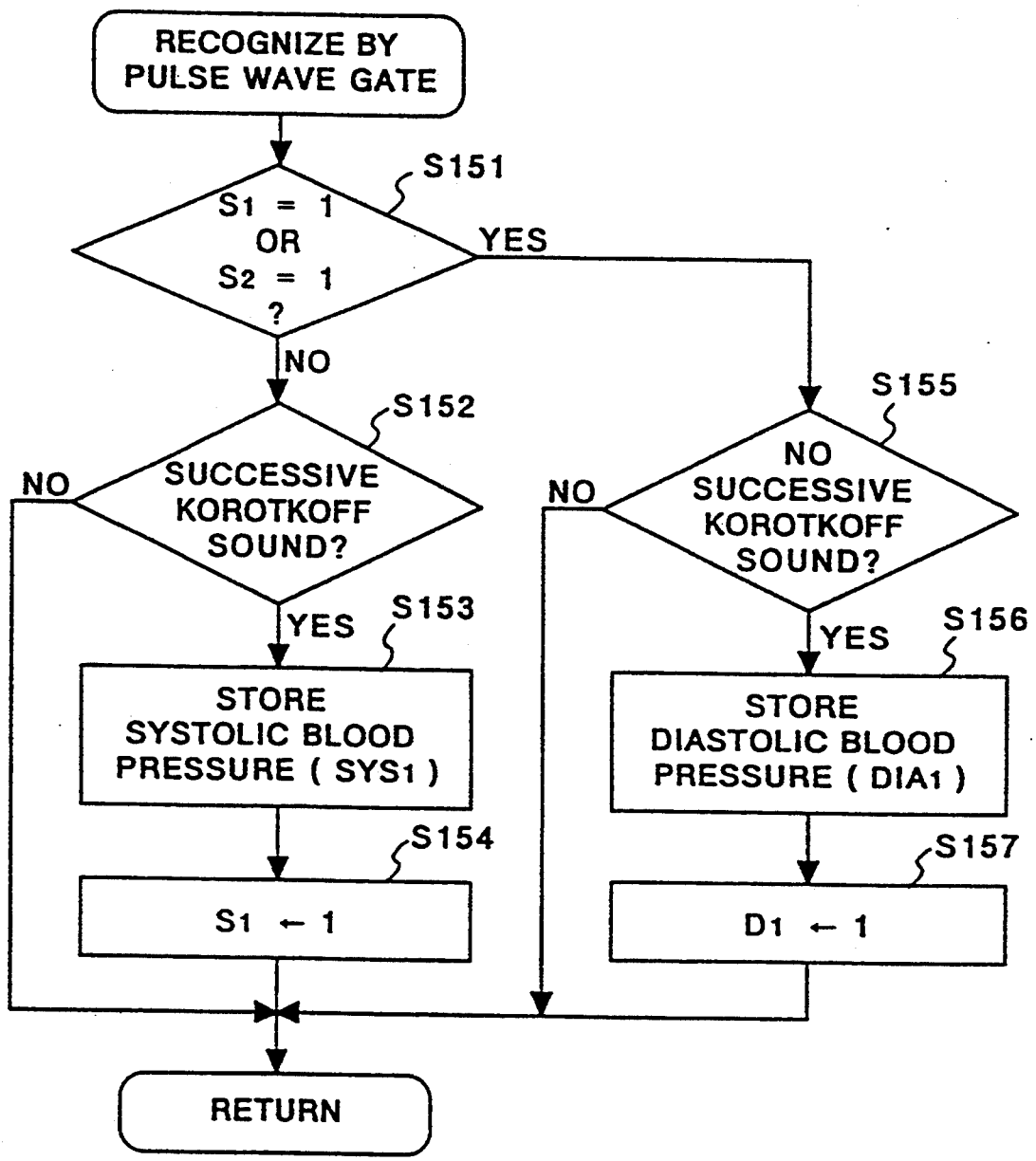

A routine of recognizing the Korotkoff sound in accordance with the oscillating pulse wave gate performed in steps S135 and S141 will be described with reference to FIG. 8C.

In step S151, whether or not flag $S_1$ or $S_2$ is "1", that is, whether or not the systolic blood pressure has been recognized, is determined. If it has not become "1", the flow advances to S152 in which it is determined whether or not two pulses of the Korotkoff sounds have been successively recognized. If it has been recognized, the flow advances to step S153 in which the present cuff pressure is stored in $SYS_1$. Then, in step S154, flag $S_1$ is set to "1" and the flow returns. If it has not been determined, the flow returns from step S152. If either of the flags has become "1", the flow advances to step S155 in which whether or not the Korotkoff sounds are successively recognized is determined. If there are no successive Korotkoff sounds, the flow advances to step S156 in which the diastolic blood pressure is stored in $DIA_1$ before the flow advances to step S157. In step S157, flag $D_1$ is set to "1" and the flow returns. If the above-described conditions are not met, the flow returns from step S155.

Figure 8D:
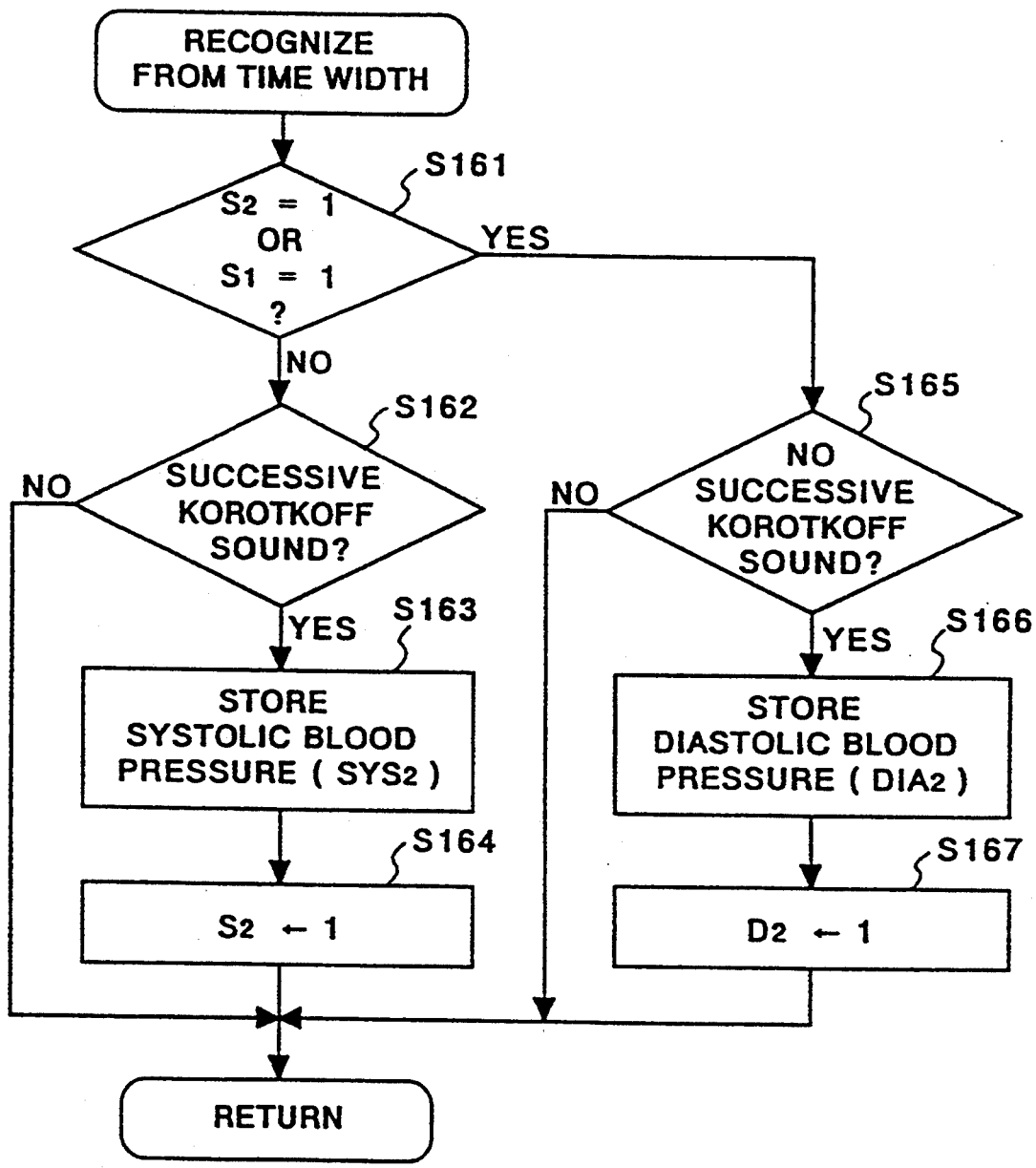

FIG. 8D illustrates a routine for recognizing the Korotkoff sound in accordance with the time width performed in steps S136 and S144. According to this routine, the recognition of the Korotkoff sound is performed in a width range from 0.35 to 2 seconds from the previous recognition of the Korotkoff sound. Furthermore, the diastolic blood pressure is stored in $SYS_2$, while the diastolic blood pressure is stored in $DIA_2$. In addition, flags $S_2$ and $D_2$ are set. Since the flow chart for this routine is arranged to be similar to that shown in FIG. 8C, it is not described in detail here.

Figure 6:
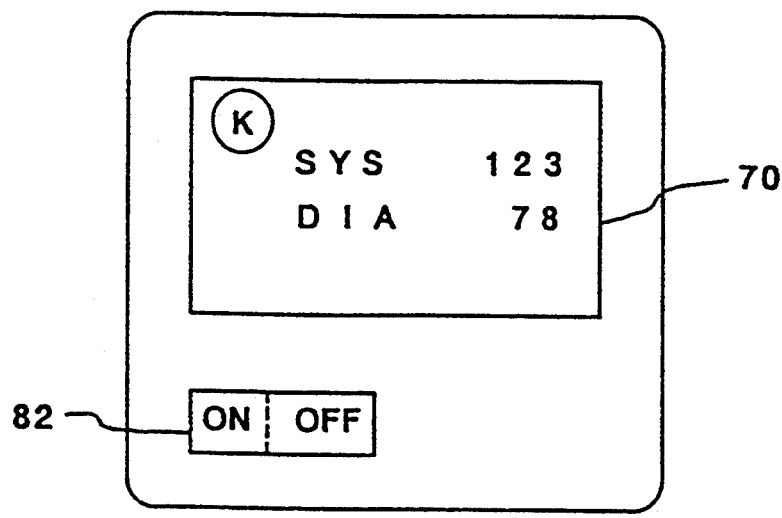
FIG. 6 illustrates an example of a display performed by the electronic sphygmomanometer according to the second embodiment of the present invention.

FIG. 6 illustrates an example of the display realized by the sphygmomanometer according to this embodiment. According to this embodiment, the case in which the recognition in accordance with only the Korotkoff sound is performed is displayed with symbol k in order to be distinguished from the case in which the recognition is made in accordance with the oscillating pulse wave gate.

The following operation for recognizing the blood pressure level in accordance with the oscillometric method by using the detected oscillation in cuff pressure may simultaneously be performed: the pressure level at the point at which the value becomes 50% or less of the maximum value is defined as the systolic blood pressure in accordance with the oscillometric method, the point being detected by a retrieval made from the point at which the level of the detected oscillation in cuff pressure becomes the maximum level toward the systolic blood pressure. On the contrary, in the retrieval made from the point of the maximum value toward the diastolic blood pressure, the cuff pressure level at the point at which the level first becomes 70% or less of the maximum value is defined as the diastolic blood pressure in accordance with the oscillometric method. The reason for simultaneously using the oscillometric method is that there arises a necessity for the diastolic pressure of a patient who is being subjected to an artificial dialysis to be recognized in accordance with the oscillometric method because of the following reason: the diastolic blood pressure cannot be recognized in accordance with the Korotkoff method because the Korotkoff sound is detected to the level below the diastolic blood pressure since blood flow noise is generated in the portion of the above-described patient who is subjected to the artery shunt and the blood flow noise overlaps the frequency band. Furthermore, the Korotkoff sound is also sometimes generated to the level below the diastolic blood pressure in accordance with individual differences due to exasperation, or in the exasperated state, causing the necessity of performing the oscillometric method to be employed to recognize the blood pressure.

A sphygmomanometer arranged to employ both the Korotkoff method and the oscillometric method may be structured in such a manner that the measurement in accordance with the oscillometric method is cancelled under the above-described condition and only the result of the measurement made in accordance with the Korotkoff method is displayed, causing the similar effect to that obtainable in accordance with this embodiment to be obtained.

As described above, in the case where the level of the oscillation in cuff pressure is too low due to the individual difference in which the K-sound is recognized although the pulse level is very low, to a case in which the cuff is wound relatively loosely or to a case in which a relatively large cuff is wound on a thin arm, an error can be prevented in the operation for recognizing the Korotkoff sound by using the oscillating pulse wave gate, which is arranged to act depending upon the synchronism with the oscillation in cuff pressure used for discriminating the noise in the Korotkoff method. Furthermore, an erroneous recognition can be prevented which may have taken place in the oscillometric method employed in the sphygmomanometer arranged to act depending upon both the Korotkoff method and the oscillometric method.

Furthermore, a structure may be employed in which another Korotkoff sound recognition method, arranged in such a manner that the measurement is made in accordance with only the Korotkoff sound prior to the recognition of the systolic blood pressure, is as well provided. As a result, the above-described structure can be easily realized. Therefore, a determination whether or not the level of the oscillating pulse wave is small can be easily and accurately made.

In addition, the blood pressure level can be easily and accurately performed in accordance with only the Korotkoff sound without an influence from respiration and sole arhythmia in such a manner that the influence of noise can be relatively satisfactorily eliminated.

According to this embodiment, an electronic sphygmomanometer is capable of accurately determining the fact that the oscillation in cuff pressure is small and overcoming the error taken place due to the above-described fact that the oscillation in cuff pressure is small.

In addition, can be electronic sphygmomanometer can be is capable of accurately determining the fact that the oscillation in cuff pressure is small, overcoming the error taken place due to the above-described fact that the oscillation in cuff pressure is small and preventing the error taken place in the measurement of the diastolic blood pressure due to a slight and sole arhythmia and respiration.

Third Embodiment

Figure 9:
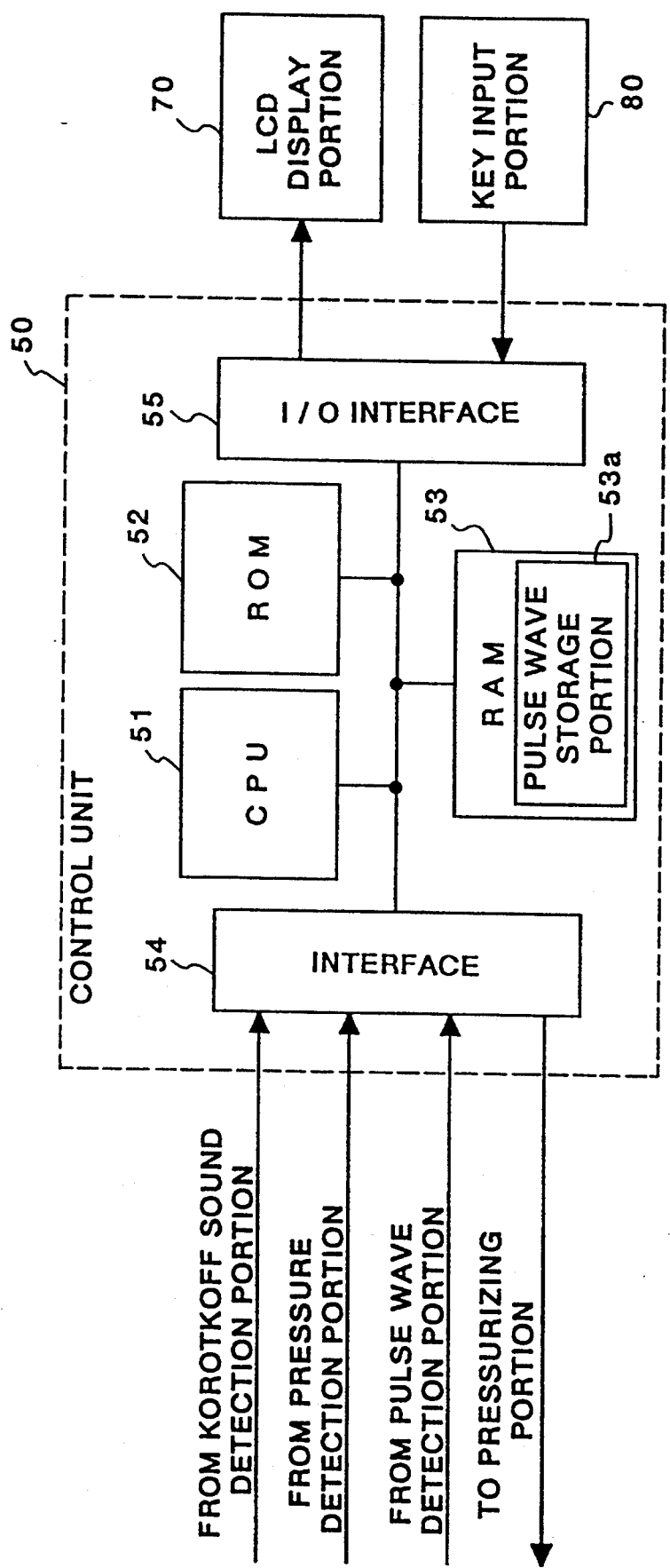
FIG. 9 is a block diagram which illustrates an essential portion of a third embodiment of the electronic sphygmomanometer according to the present invention.

FIG. 9 is a block diagram which illustrates an essential portion of a third embodiment of an electronic sphygmomanometer according to the present invention.

The structure of the electronic sphygmomanometer according to this embodiment is arranged to be similar to that according to the first and the second embodiments except for the structure in which the RAM 53 has a oscillating pulse wave storage portion 53a for storing the maximum height of the oscillating pulse wave and at least five oscillating pulse waves in the vicinity of the generation and the disappearance points of the Korotkoff sound, the maximum height and the five pulses being allowed to coincide with the cuff. Therefore, the same portions are omitted from illustration.

Example of Measurement at Reduced Pressure

The generation and disappearance points of the Korotkoff sound are successively measured by the electronic sphygmomanometer having the oscillating pulse wave detection portion 30. The above-described electronic sphygmomanometer has a function of defining the cuff pressure level at the generation point as the systolic blood pressure or defining the cuff pressure level at the disappearance point as the diastolic blood pressure. Furthermore, the above-described electronic sphygmomanometer has a function of defining the cuff pressure at the generation point as the diastolic blood pressure or defining the cuff pressure at the disappearance point as the systolic blood pressure. In addition, the above-described electronic sphygmomanometer has a function of storing the level of each of five oscillating pulse waves in the vicinity of the generation and disappearance points of the Korotkoff sound and the maximum level of the oscillating pulse wave. The thus-arranged electronic sphygmomanometer is arranged in such a manner that the validity of the systolic blood pressure and the diastolic blood pressure points recognized in accordance with the following flow and the Korotkoff method is confirmed.

Figure 10:
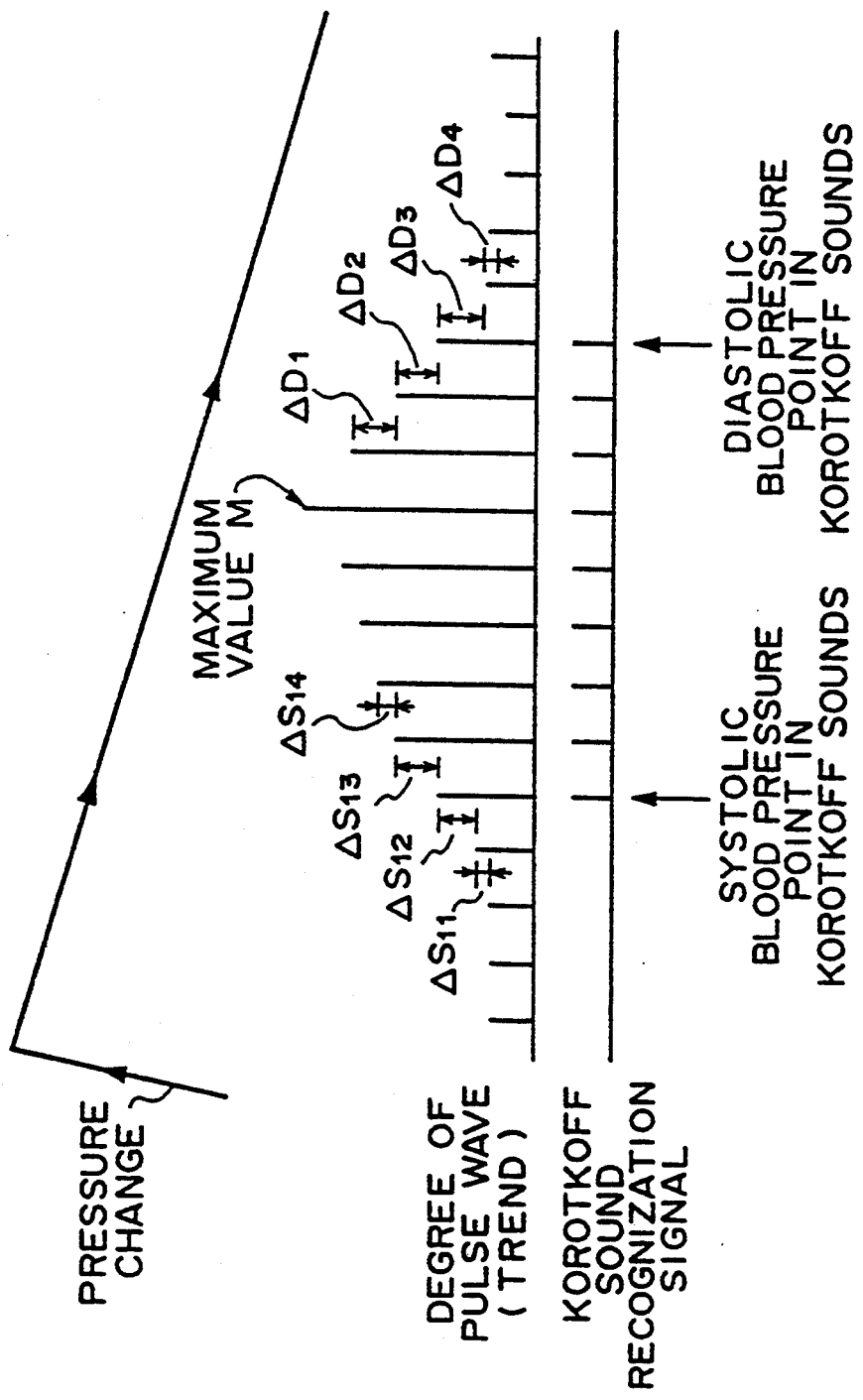
FIG. 10 illustrates the principle of the measurement performed only when the pressure is reduced.

FIG. 10 illustrates the principle of the measurement of the electronic sphygmomanometer according to the present invention which measures the blood pressure level when the pressure is being reduced.

The first point of the Korotkoff sounds which have been successively generated due to the pressure reduction after the application of pressure is defined as the systolic blood pressure. The difference in the height of the oscillating pulse waves in the vicinity of the first point are successively arranged to be $\Delta S_{11}$, $\Delta S_{12}$, $\Delta S_{13}$ and $\Delta S_{14}$. In accordance with the height of the wave at the systolic blood pressure and the above-described difference values, the validity of the systolic blood pressure point is confirmed.

The first point when the Korotkoff sound disappears successively is arranged to be the systolic blood pressure. The differences in the heights of the five oscillating pulse waves in the vicinity of the above-described point are successively arranged to be $\Delta D_1$, $\Delta D_2$, $\Delta D_3$ and $\Delta D_4$. The validity of the diastolic blood pressure is confirmed in accordance with the height of the wave at the systolic blood pressure and the above-described difference values.

The operation of the electronic sphygmomanometer according to this embodiment will be described in detail with reference to flow charts shown in FIGS. 11 to 13.

Figure 11:
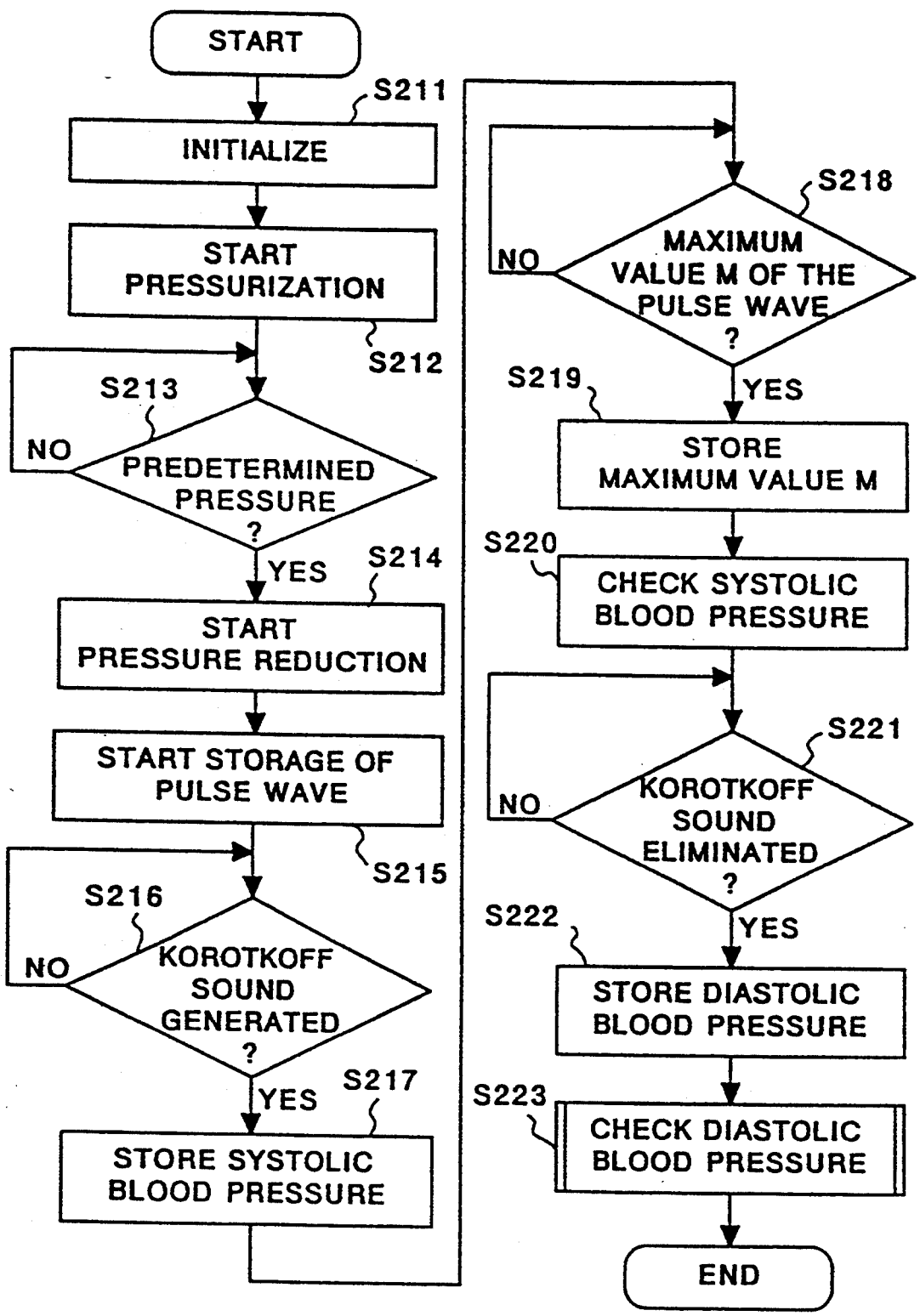
FIG. 11 is a flow chart which illustrates the flow of the operation performed in accordance with the principle shown in FIG. 10.

FIG. 11 illustrates the main flow of the electronic sphygmomanometer according to this embodiment.

In step S211, the initialization of the electronic sphygmomanometer is performed in which the pressure is set to zero or the like. In step S212, the pressure application is started, and in step S213, it is confirmed that whether or not the pressure has been raised to a predetermined pressure higher than the systolic blood pressure. If the pressure has been raised to the predetermined pressure, the confirmation is stopped and the flow advances to step S214 in which the pressure reduction is started. Simultaneously with the start of the pressure reduction, the oscillating pulse wave commences to be stored in the oscillating pulse wave storage portion 53a in step S215. In step S216, the timing at which the Korotkoff sounds are successively generated is found, and the thus found point is stored as the systolic blood pressure.

In step S218, whether or not the subject oscillating pulse wave is the maximum value of the oscillating pulse wave is confirmed. In step S219, the maximum wave height M is stored, and the validity is confirmed in accordance with the height of the wave at the systolic blood pressure point and the differences in the height of the waves in the vicinity of the systolic blood pressure.

Figure 12A:
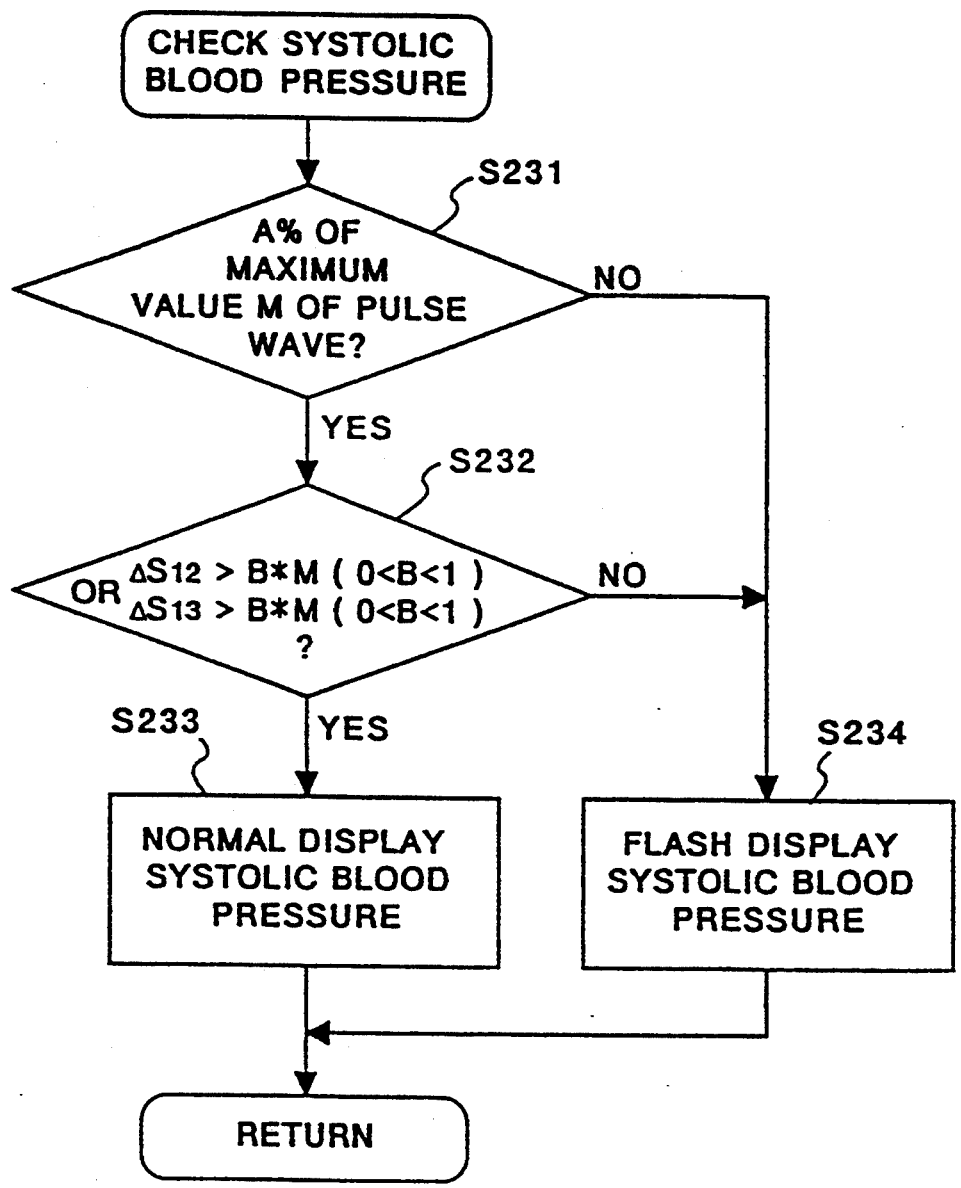

FIGS. 12A and 12B are flow charts which illustrate two examples for checking the systolic blood pressure performed in step S220.

In step S231, it is confirmed that whether or not the height of the oscillating pulse wave at the systolic blood pressure point is A% (for example, 30%) or more of the maximum wave height stored in step S219. If it is not A% or more, the validity of the systolic blood pressure thus measured is suspicious. Therefore, the flow advances to step S234 in which the systolic blood pressure is displayed in a flash manner. If it is A% or more, the flow advances to step S232 in which it is determined whether or not difference $\Delta S_{12}$ or $\Delta S_{13}$ is larger than the product of the maximum value M and predetermined value B (for example, B=0.1, 0<B<1). If it is smaller than the above-described product, the flow advances to step S234 in which the systolic blood pressure is displayed in the flash manner. If the wave height is A% or more of the maximum value M and also the difference $\Delta S_{12}$ or $\Delta S_{13}$ is larger than the product of the maximum value M and predetermined value B, it is determined that the measured systolic blood pressure is valid and the flow advances to step S233 in which the systolic blood pressure is displayed in a normal manner.

According to the flow chart shown in FIG. 12B, the checking operation performed in step S232 shown in FIG. 12A is replaced by a checking operation shown in step S236. In step S236, the following relationships are held:

$\alpha_1 = \Delta S_{11}/\Delta S_{12}$ $\beta_1 = \Delta S_{12}/\Delta S_{13}$ $\gamma_1 = \Delta S_{13}/\Delta S_{14}$ Referring back to FIG. 11, the flow advances to step S221 in which the disappearance of the Korotkoff sounds is checked successively and the time at which the Korotkoff sound has disappeared is stored as the diastolic blood pressure point in step S222. Then, the validity of the thus stored diastolic blood pressure is checked in step S223.

Figure 13A:
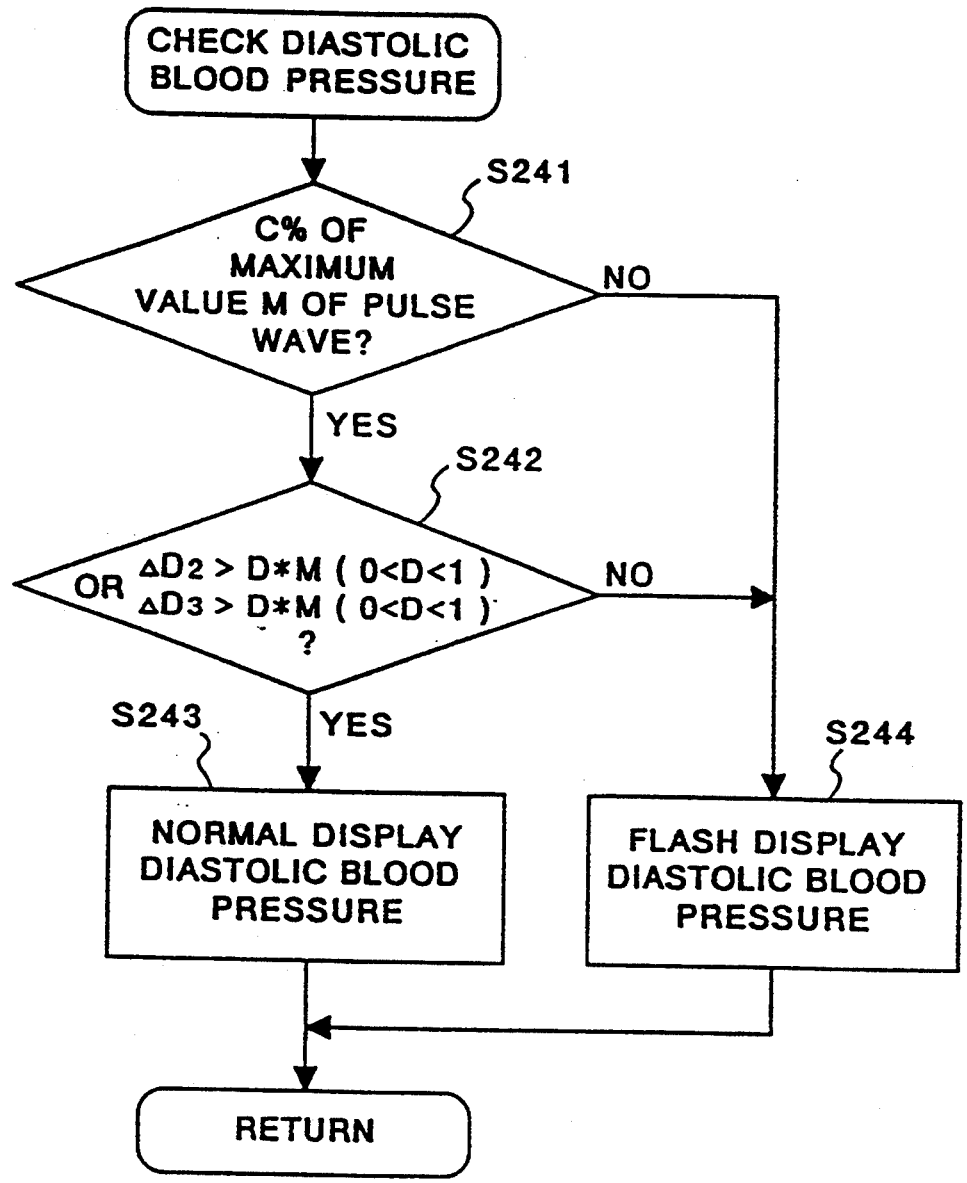
FIGS. 13A and 13B are flow charts which illustrate the checking routine of the diastolic blood pressure according to the example shown in FIG. 10.
Figure 13B:
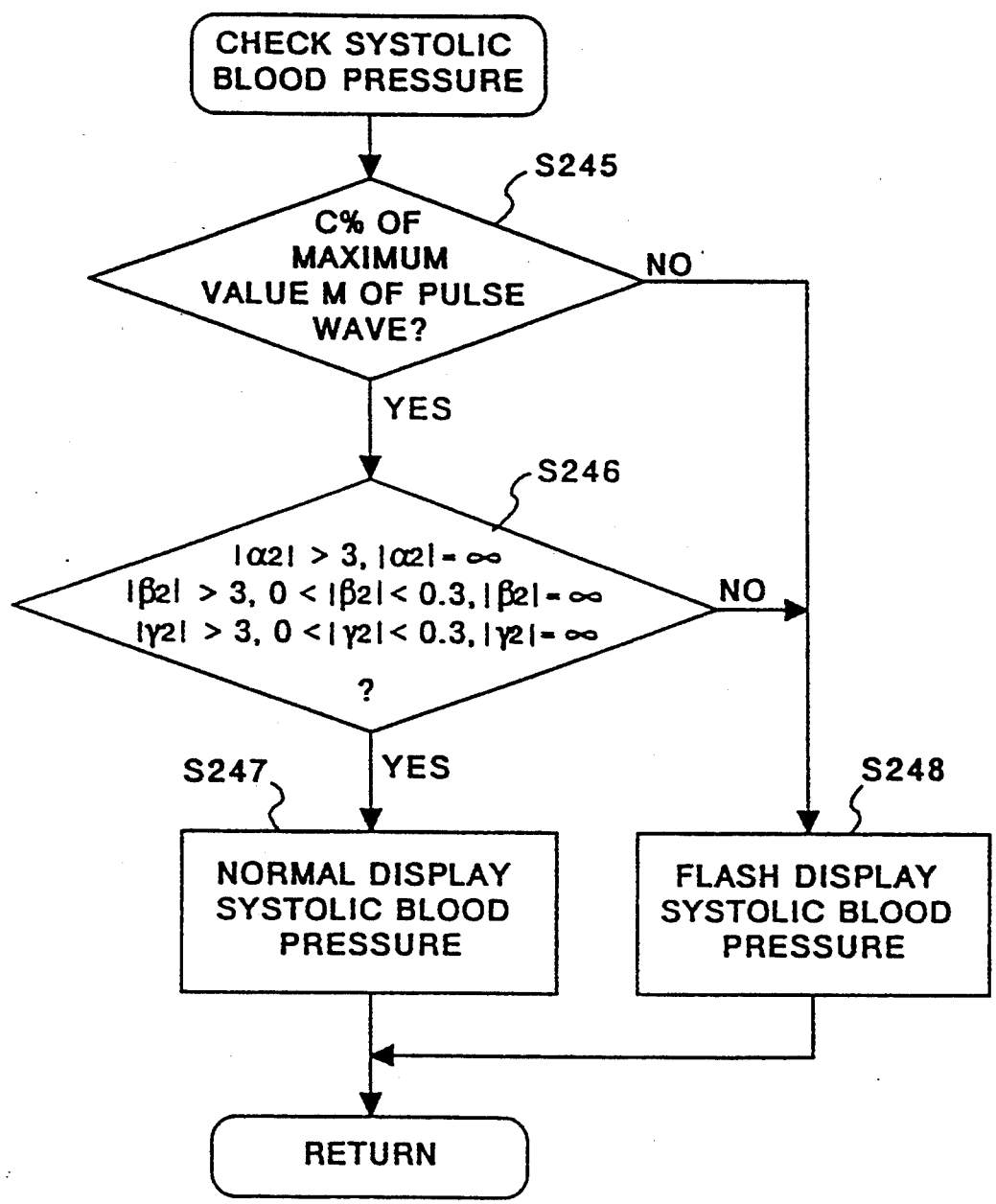

FIGS. 13A and 13B illustrate two example of the checking operation of the diastolic blood pressure performed in step S223.

In step S241, it is confirmed whether or not the wave height of the oscillating pulse wave at the diastolic blood pressure point is C% (for example, 40%) or more of the maximum wave height M stored in step S219. If it is not C% or more, it is determined that the validity of the diastolic blood pressure is suspicious and the flow advances to Step S244 in which the diastolic blood pressure is displayed in the flash manner. If it is larger than C%, the flow advances to step S242 in which it is determined whether or not difference value $\Delta D_2$ or $\Delta D_3$ is larger than the product of the maximum value M and the predetermined value D (for example, D=0.1, 0<D<1). If it is larger than the above-described product, the flow advances to step S244 in which the diastolic blood pressure is displayed in the flash manner. In only the case where the wave height is larger than C% of the maximum value M and also the difference value $\Delta D_2$ or $\Delta D_3$ is larger than the product of the maximum value M and the predetermined value D, the flow advances to step S243 in which the diastolic blood pressure is displayed in a normal manner.

FIG. 13B illustrates a flow arranged by replacing step S242 shown in FIG. 13A by step S246.

According to step S246, the following relationships are held:

$$\alpha_2 = \Delta D_2 / \Delta D_1$$

$$\beta_2 = \Delta D_3 / \Delta D_2$$

$$\gamma_2 = \Delta D_4 / \Delta D_3$$

Example of Measurement at Pressure Application/Reduction

An electronic sphygmomanometer, arranged to measure the systolic and diastolic blood pressures at the time of the pressure application and to again measure the diastolic blood pressure at the time of the pressure reduction in accordance with the Korotkoff method, acts in accordance with the following flow arranged in such a manner: the diastolic blood pressure measured at the pressure application and the diastolic blood pressure measured at the pressure reduction are subjected to a comparison. Then, if the difference between the above-described two diastolic blood pressures is a score of mmHg or less, it is measured at a pressure reduction rate smaller than the rate of the pressure application since the blood pressure change is usually a score of mmHg for the body of a person who is keeping quiet. Therefore, the diastolic blood pressure at the time of the pressure reduction is displayed since it is further probable. In the case where the difference is larger than a score of mmHg, the diastolic blood pressure is similarly checked, and then the diastolic blood pressure which is more valid is displayed. If it has been determined that both of them are valid, the diastolic blood pressure level at the time of the pressure reduction is displayed as the diastolic blood pressure because of the above-described reason.

The oscillating pulse wave placed prior to the generation point due to the Korotkoff sound by one pulse is experientially known to be relatively stable. Therefore, it is confirmed whether or not the rate of the above-described oscillating pulse wave and the maximum value of the oscillating pulse wave is in a certain range so that the validity of the diastolic blood pressure at the time of the pressure application is confirmed.

Figure 14:
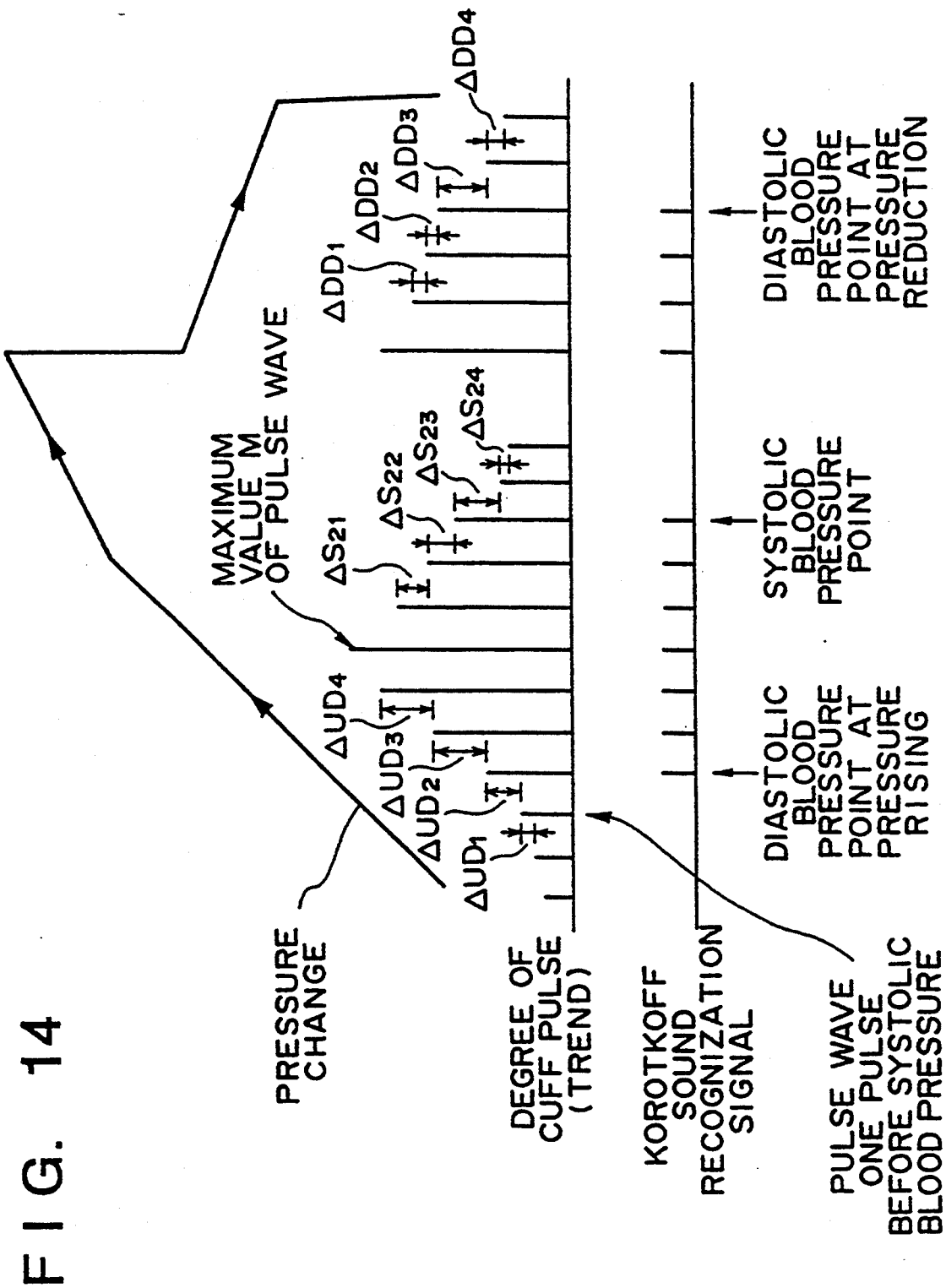
FIG. 14 illustrates the principle of an example arranged to measure the blood pressure at the times of the pressure application and reduction.

FIG. 14 illustrates the principle of a measurement capable of reliably measuring the blood pressure by measuring the blood pressure at the time of the pressure reduction and the pressure application.

First, the generation of the Korotkoff sound is arranged to be the diastolic blood pressure point at the time of the pressure application, while the disappearance of the Korotkoff sound is arranged to be the systolic blood pressure point. Furthermore, the disappearance of the Korotkoff sound at the time of the pressure reduction is arranged to be the diastolic blood pressure point at the time of the pressure reduction. Furthermore, five oscillating pulse waves in the vicinity of each of the above-described points are stored so as to check the validity of the blood pressure level in accordance with the wave height at each of the points, the presence of the oscillating pulse wave prior to each of the points or the differences in the heights of the oscillating pulse waves. As for the diastolic blood pressure, a further accurate measurement can be performed at the time of the pressure reduction in accordance with the diastolic blood pressure at the time of the pressure application. In addition, the fear that the measurement of the diastolic blood pressure cannot be performed is overcome by performing the measurement operations two times.

Figure 15:
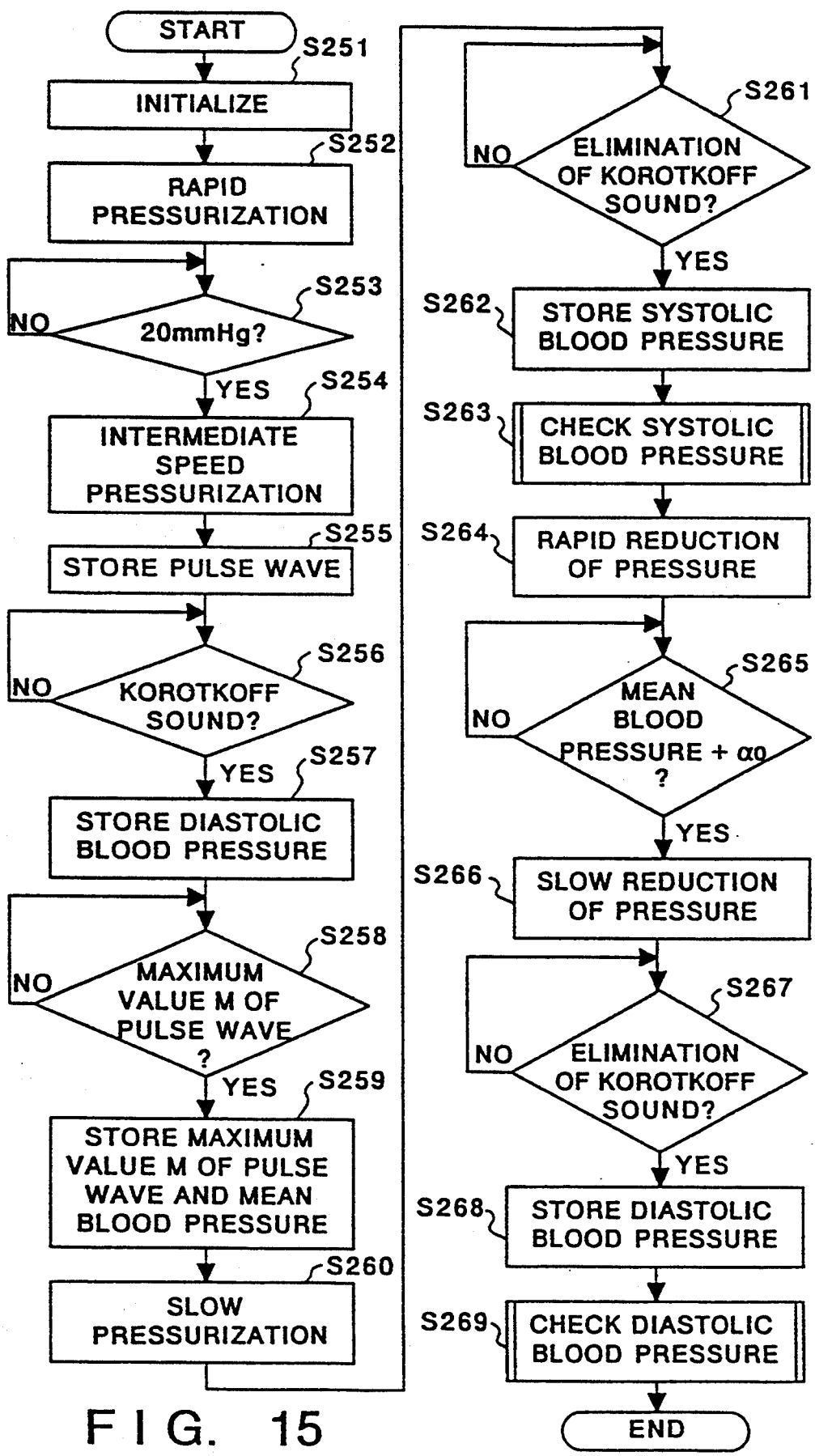
FIG. 15 is a flow chart which illustrates the flow of the operation performed by the structure shown in FIG. 14.
Figure 16:
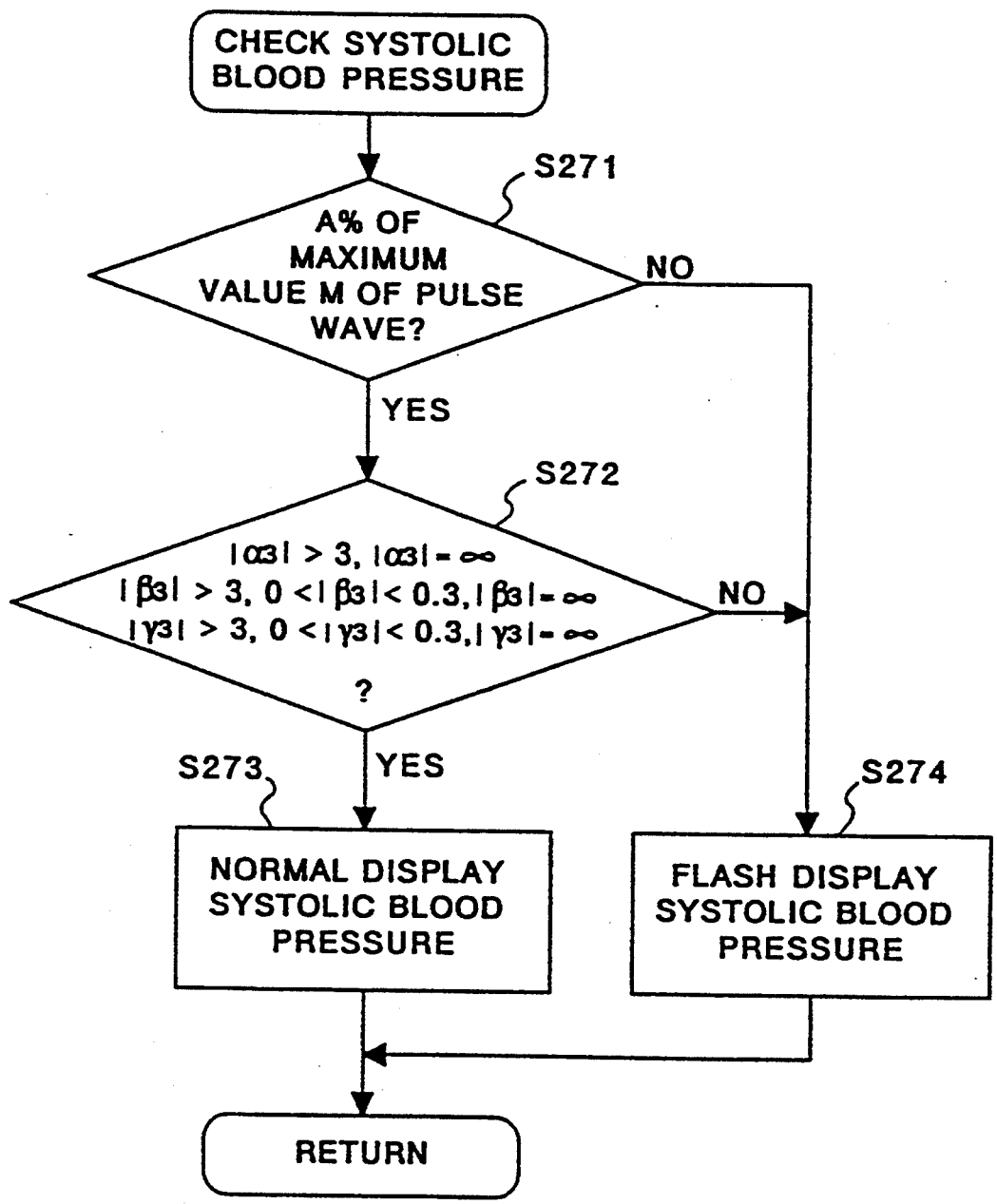
FIG. 16 is a flow chart which illustrates the checking routine of the systolic blood pressure performed by the structure shown in FIG. 14.
Figure 17A:
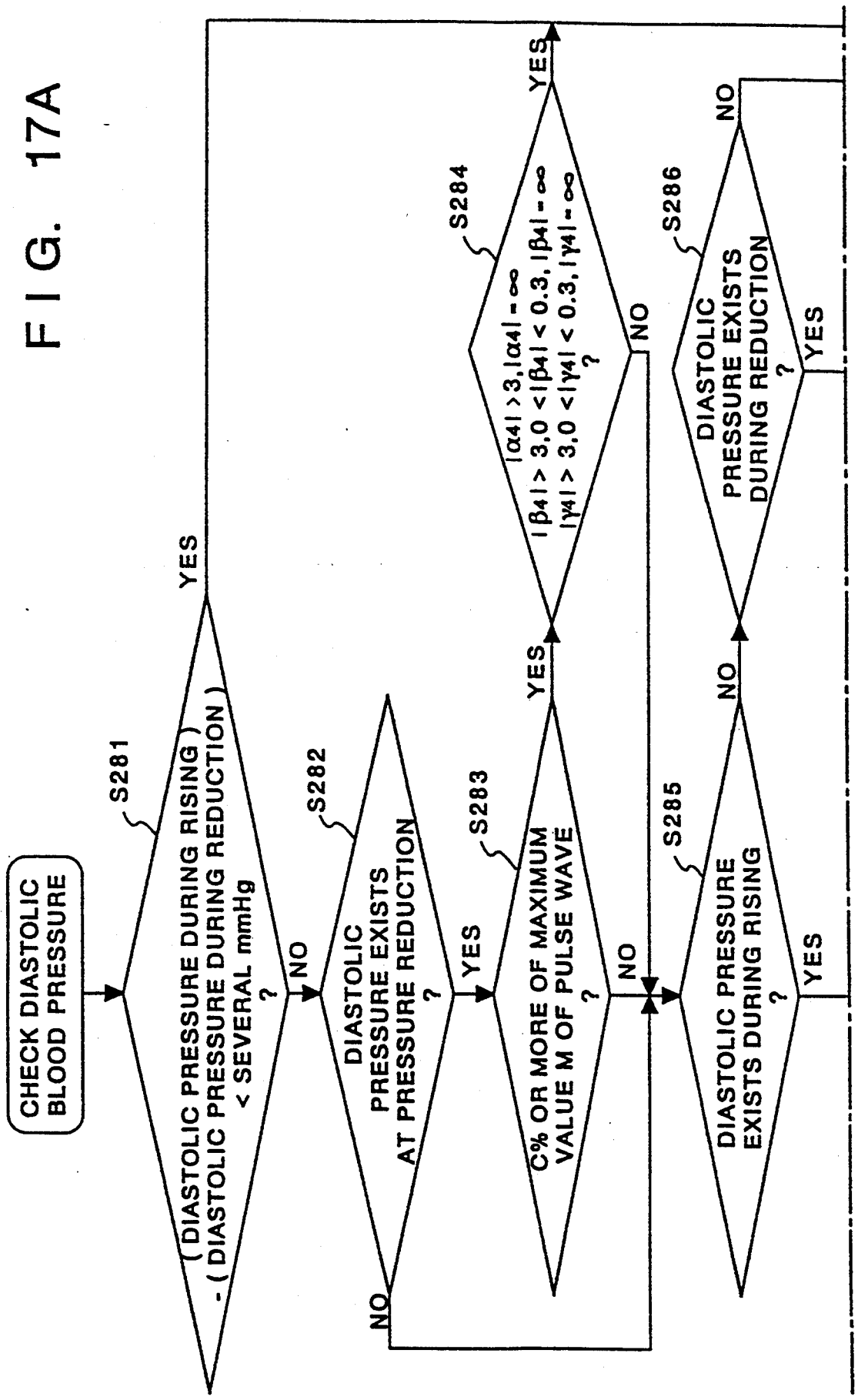
FIG. 17 is a flow chart which illustrates the checking routine of the diastolic blood pressure performed by the structure shown in FIG. 14.
Figure 17B:
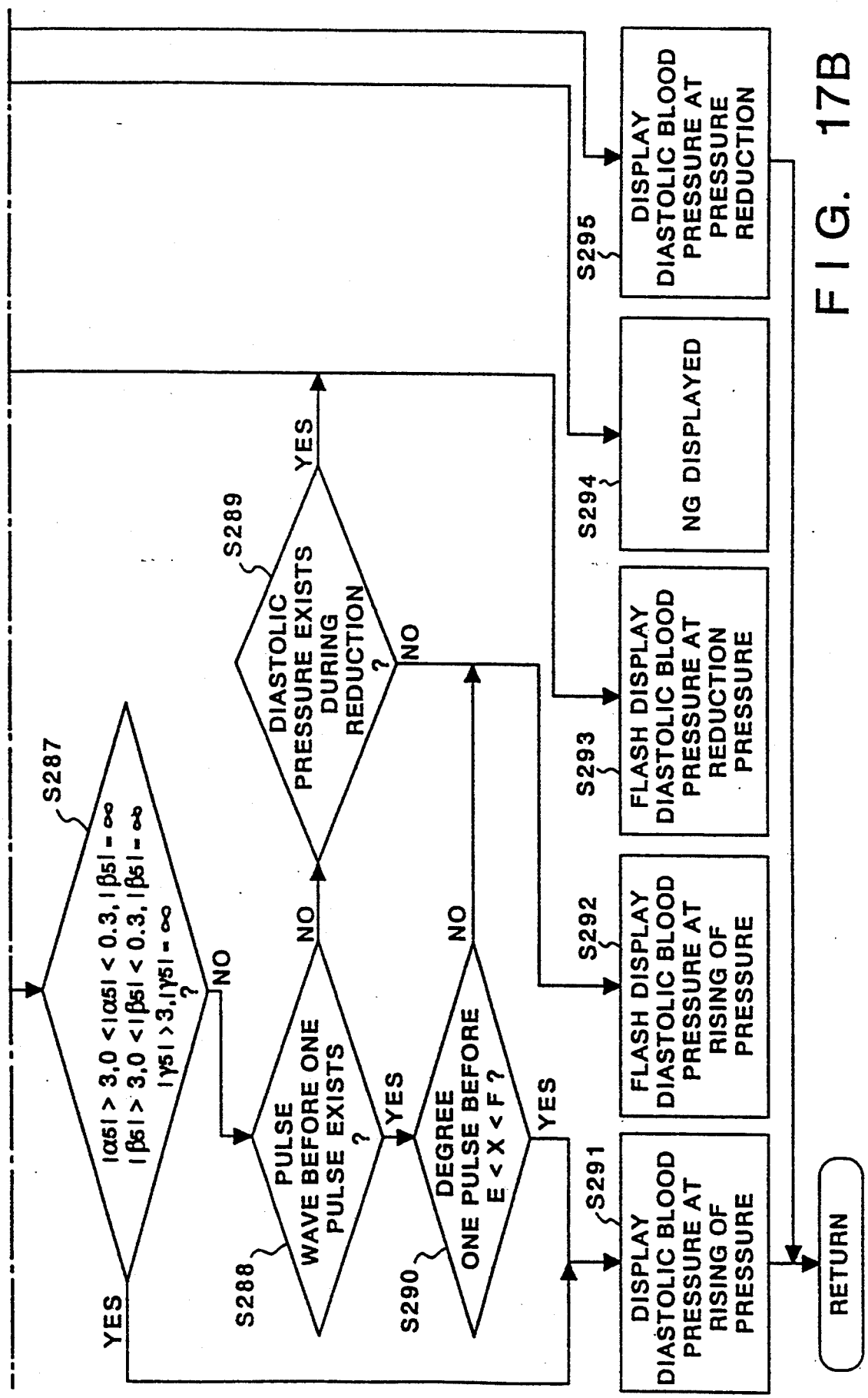

FIGS. 15 to 17 are flow charts which illustrate the operation of the electronic sphygmomanometer according to this embodiment.

FIG. 15 illustrates the main routine.

First, in step S251, the initialization, for example, the zero setting of the pressure level, of the electronic sphygmomanometer according to this embodiment is performed. In steps S252 and S253, the pressure is rapidly raised up to 20 mmHg. When the pressure has been raised to 20 mmHg, the pressure application is switched to a medium application mode in S254 and the flow advances to step S255 in which the oscillating pulse wave is, corresponding to the cuff pressure, stored in the oscillating pulse wave storage portion 53a.

In step S256, the generation of the successive Korotkoff sounds is confirmed. If it has been generated, the flow advances to step S257 in which the first point is stored as the diastolic blood pressure at the time of the pressure application. In step S258, the maximum value M of the oscillating pulse wave is detected, and the maximum value M and the mean blood pressure are stored in step S259. After the maximum value M of the oscillating pulse wave has been generated, the flow advances to step S260 in which the pressure application is switched to a low application rate. Then, in step S261, the disappearance of the Korotkoff sound is checked, and the disappearance point is arranged to be the systolic blood pressure point in step S262. Then, in step S263, the systolic blood pressure is confirmed.

FIG. 16 is a flow chart for checking the systolic blood pressure performed in step S263.

In step S271, it is confirmed that whether or not the height of the oscillating pulse wave at the systolic blood pressure point is A% or more of the maximum wave height stored in step S259. If it is not A% or more, the validity of the systolic blood pressure thus measured is suspicious. Therefore, the flow advances to step S274 in which the systolic blood pressure is displayed in a flash manner. If it is A% or more, the flow advances to step S272 in which the checking is performed in accordance with the differences in the adjacent five oscillating pulse waves. If it is not within the predetermined range, the flow advances to step S274 in which the systolic blood pressure is displayed in the flash manner.

In step S272, the following relationships are held:

$$\alpha_3 = \Delta S_{22}/\Delta S_{21}$$

$$\beta_3 = \Delta S_{23}/\Delta S_{22}$$

$$\gamma_3 = \Delta S_{24}/\Delta S_{23}$$

If it is A% or more and in the predetermined range, the systolic blood pressure is displayed in a normal manner in step S273.

Then, the flow returns to step S264 shown in FIG. 15, and the pressure is rapidly reduced to a level higher than the mean blood pressure stored in step S259 by a level $\alpha_0$ (for example, 20 mmHg) in steps S264 and S265. When the pressure has been reduced to (Mean blood pressure+$\alpha_0$), the flow advances to step S266 in which the pressure reduction rate is switched to the constant low rate before the flow advances to step S267 in which the disappearance of the Korotkoff sound is checked. In step S268, the disappearance point is arranged to be the diastolic blood pressure point at the time of the pressure reduction, and its validity is, together with the diastolic blood pressure point at the time of the pressure application stored in step S257, checked in step S269.

FIG. 17 is a flow chart which illustrates the flow of the checking operation of the diastolic blood pressure performed in step S269.

In step S281, the difference between the diastolic blood pressure at the time of the pressure application and the diastolic blood pressure at the time of the pressure reduction is calculated and it is checked whether or not the difference is smaller than several mmHg. If it is smaller than several mmHg, the diastolic blood pressure at the time of the pressure reduction is displayed since it is more accurate value. If the difference in the pressure level between the pressure application and the pressure reduction is a large level, the flow advances to step S282 in which whether or not there is the result of the measurement of the diastolic blood pressure at the time of the pressure reduction is checked. If it is present, the flow advances to steps S283 and S284 in which the validity of the diastolic blood pressure at the time of the pressure reduction is checked. If it is determined that it is valid, the flow advances to step S295 in which the diastolic blood pressure at the time of the pressure reduction is displayed.

In step S284, the following relationships are held:

$$\alpha_4 = \Delta DD_2/\Delta DD_1$$

$$\beta_4 = \Delta DD_3/\Delta DD_2$$

$$\gamma_4 = \Delta DD_4/\Delta DD_3$$

If there is not diastolic blood pressure at the time of the pressure reduction or if it is not valid, the flow advances to step S285 in which it is determined whether or not there is the diastolic blood pressure at the time of the pressure application. If it is not present, the flow advances to step S286 in which the presence of the diastolic blood pressure is again checked. If it is not present, there is no diastolic blood pressure, causing the flow to be brought to step S294. In step S294, the fact that the measurement of the diastolic blood pressure cannot be performed is displayed. If there is the diastolic blood pressure at the time of the pressure reduction, the flow advances to step S293 in which a fact that the validity of the diastolic blood pressure at the time of the pressure reduction is suspicious is displayed by the flash manner.

If there is a diastolic blood pressure at the time of the pressure application, the validity of it is checked in steps S287, S288 and S290.

In step S287, the following relationships are held:

$$\alpha_5 = \Delta UD_1/\Delta UD_2$$

$$\beta_5 = \Delta UD_2/\Delta UD_3$$

$$\gamma_5 = \Delta UD_3/\Delta UD_4$$

In the case where it is in the range shown in step S287 and in the case where the oscillating pulse wave which is previous by one pulse is present and its height is within the predetermined range, the flow advances to step S291 in which the diastolic blood pressure at the time of the pressure application is displayed as a valid value. If there is no oscillating pulse wave prior by one pulse, the flow advances to step S289 in which whether or not there is the diastolic blood pressure at the time of the pressure reduction is determined. It it is present, the flow advances to step S293 in which it is displayed in the flash manner. If it is not present, the flow advances to step S292 in which the diastolic blood pressure at the time of the pressure application is displayed in the flash manner. Even if the oscillating pulse wave prior by one pulse is present, the diastolic blood pressure at the time of the pressure application is displayed in the flash manner if it is not included in the predetermined range (larger than E and also smaller than F).

According to this embodiment, a reliable electronic sphygmomanometer can be provided since an accurate checking is performed.

Furthermore, since the blood pressure levels at the time of the pressure application and the pressure reduction are obtained, a reliable electronic sphygmomanometer can be provided since an accurate checking is performed.

That is, if there arises the error in the measurement operation due to the noise caused from the friction with the rubber tube or the clothes, the re-measurement can be caused to be performed. Therefore, the recognition of the erroneous result by the operator can be assuredly prevented.

Although the invention has been described in its referred form with a certain degree of particularity the present invention is not limited to the particular above descriptions, and it is to be understood that the present disclosure of the preferred form can be changed in the details of construction and the combination and arrangement of parts, to without departing from the spirit and the scope of the invention as hereinafter claimed.

What is claimed is:

1. In an electronic sphygmomanometer, wherein a cuff is arranged to be placed on a body part of a person, the improvement comprising:
   first time zone determining means for determining a first time zone, in which a Korotkoff sound is expected to occur, in accordance with a cuff pressure oscillation during a depressurizing of the cuff;

blood pressure recognizing means for recognizing a blood pressure in accordance with a generation of a Korotkoff sound in the first time zone determined by said first time zone determining means; and time zone determination stopping means for stopping the determination of the first time zone performed by said first time zone determining means when a condition of detected cuff pressure oscillations, before a recognition point of a systolic blood pressure, meets a predetermined condition.

2. An electronic sphygmomanometer according to claim 1, wherein said time zone determination stopping means includes means for stopping the determination of the first time zone when a number of cuff pressure oscillations detected before a detection of a first Korotkoff sound is less than a predetermined number of cuff pressure oscillations.

3. An electronic sphygmomanometer according to claim 1, further comprising:

second time zone determining means for determining a second time zone having a predetermined time width, in which a next Korotkoff sound is expected to occur, after a recognition point of a present Korotkoff sound; and wherein in a case where the determination of the first time zone is stopped by said time zone determination stopping means, said blood pressure recognizing means recognizes a blood pressure by using the second time zone determined by said second time zone determining means.

* * * * *

UNITED STATES PATENT AND TRADEMARK OFFICE
CERTIFICATE OF CORRECTION

PATENT NO. : 5,447,162
DATED : September 5, 1995
INVENTOR(S) : Takahiro SOUMA

It is certified that error appears in the above-indentified patent and that said Letters Patent is hereby corrected as shown below:

Title page, Item [19], change "Shinomiya et al." to --Souma--.

Item [75] Inventors:
      line 1, delete "Tsutomu Shinomiya;"
      line 2, delete "both".

Column 1, line 24, after "over" insert --an--;
         line 25, before "through" insert --, or--;
         line 28, change "he" to --the--;
         last line, change "drawback" to --drawbacks--.

Column 9, line 38, change "The" (first occurrence) to --In the--.

Column 10, line 45, change "means" to --areas--.

Column 11, line 25, change "not" to --been--;
         line 46, after "and" insert --also--.

UNITED STATES PATENT AND TRADEMARK OFFICE
CERTIFICATE OF CORRECTION

PATENT NO.  : 5,447,162
DATED       : September 5, 1995
INVENTOR(S) : Takahiro SOUMA It is certified that error appears in the above-indentified patent and that said Letters Patent is hereby corrected as shown below:

Column 12, line 29, change "In" to
    --As shown in Fig. 8A, in--;
    same line, change "sphygmomanometerometer" to
    --sphygmomanometer--;
    line 45, before "as" insert --which,--;
    line 67, "change "no step" to --to step--.

Column 14, line 63, change "can be" (first occurrences) to
    --the--;
    line 64, delete "can be".

Column 19, line 41, before "more" insert --a--.

Column 20, line 55, after "particularity" insert --,--;
    line 61, delete --to--.

Signed and Sealed this

Fifteenth Day of July, 1997

Attest:

BRUCE LEHMAN

*Attesting Officer*   *Commissioner of Patents and Trademarks*